(12) United States Patent
Nakamura et al.

(10) Patent No.: US 7,521,205 B2
(45) Date of Patent: Apr. 21, 2009

(54) GENES AND POLYPEPTIDES RELATING TO PROSTATE CANCERS

(75) Inventors: Yusuke Nakamura, Yokohama (JP); Toyomasa Katagiri, Shinagawa-ku (JP); Hidewaki Nakagawa, Shinagawa-ku (JP); Shuichi Nakatsuru, Saitama (JP)

(73) Assignee: Oncotherapy Science, Inc., Kanagawa (JP)

( * ) Notice: Subject to any disclaimer, the term of this patent is extended or adjusted under 35 U.S.C. 154(b) by 320 days.

(21) Appl. No.: 10/529,381

(22) PCT Filed: Sep. 22, 2003

(86) PCT No.: PCT/JP03/12074

§ 371 (c)(1),
(2), (4) Date: Nov. 28, 2005

(87) PCT Pub. No.: WO2004/031231

PCT Pub. Date: Apr. 15, 2004

(65) Prior Publication Data

US 2006/0160991 A1    Jul. 20, 2006

Related U.S. Application Data

(60) Provisional application No. 60/414,873, filed on Sep. 30, 2002.

(51) Int. Cl.
*C12P 21/06* (2006.01)
(52) U.S. Cl. .................. 435/69.1; 530/350; 536/23.5; 435/320.1; 435/325
(58) Field of Classification Search ................. 530/350; 536/23.5, 23.1; 435/320.1, 69.1; 436/325; 514/12
See application file for complete search history.

(56) References Cited

FOREIGN PATENT DOCUMENTS

| JP | 2002-010789 A | 1/2002 |
|---|---|---|
| WO | WO 99/64631 A1 | 12/1999 |
| WO | WO 01/51628 A2 | 7/2001 |
| WO | WO 03/066821 A2 | 8/2003 |

OTHER PUBLICATIONS

Terman et al (Cell (2002) vol. 109, pp. 887-900.*
GenBank accession NT_024524.7 gl:17475964, 2001.*
Skolnick et al. (Trends in Biotechnology 2000; 18: 34-39).*
Verma et al. (Nature 1997, 389: 239-242).*
Amalfitano et al. (Current Gene Therapy 2002, 2: 111-133).*
Pandha et al. (Current Opinion in Investigational Drugs 2000; 1(1): 122-134).*
Gura (Science. 1997; 278: 1041-1042).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Boehringer Mannheim Biochemicals, 1994 Catalog (No. 1034 731/ 1006 924), p. 93.*
Ashida et al. (Cancer Res. Sep. 1, 2004; 64 (17): 5963-5972).*
Ashida et al. (Clin. Cancer Res. May 1, 2006; 12 (9): 2767-2773).*
Edwards, J.B.D.M. et al.; "EST and encoded human protein"; *EMBL Database*; Sep. 20, 2002; Acession No. BD110979 (from JP 2002010789 A).
Lillie, J. et al.; "Human breast cancer expressed polynucleotide 18890"; *EMBL Database*; Dec. 7, 2001; Accession No. AAL26433 (from WO 2001/051628 A2).
Lin, Shi-Lung et al.; "A novel mRNA-cDNA interference phenomenon for silencing bcl-2 expression in human LNCaP cells"; *Biochem. Biophys. Res. Comm.*; 2001; pp. 639-644; vol. 281; Academic Press.
Ohara, O. et al.; "*Homo sapiens* mRNA for KIAA0750 protein, complete cds"; *EMBL Database*; Nov. 17, 1998; Accession No. AB018293.
Suzuki, Takahiro et al.; "MICAL, a novel CasL interacting molecule, associates with vimentin"; *J. Biol. Chem.*; Apr. 26, 2002; pp. 14933-14941; vol. 277, No. 17.
Terman, Jonathan R. et al.; "MICALs, a family of conserved flavoprotein oxidoreductases, function in plexin-mediated axonal repulsion"; *Cell*; Jun. 28, 2002; pp. 887-900; vol. 109.
Anazawa, Y., et al.; Database; GenBank; AB113650; "PCOTH, A Novel Gene Overexpressed In Prostate Cancers, Promotes Prostate Cancer Cell Growth Through Phosphorylation Of Oncoprotein TAF-Ibeta/SET"; Oct. 5, 2006.

* cited by examiner

*Primary Examiner*—Stephen L Rawlings
(74) *Attorney, Agent, or Firm*—Townsend and Townsend and Crew LLP

(57) ABSTRACT

The present application provides novel human gene MICAL2-PV whose expression is markedly elevated in prostate cancers. Furthermore, it provides polypeptides encoded by the gene as well as polypeptides encoded by PCOTH which expression was also discovered to be elevated in prostate cancers. The genes and polypeptides encoded by the genes can be used, for example, in the diagnosis of prostate cancers, as target molecules for developing drugs against the disease, and for attenuating cell growth of prostate cancer.

2 Claims, 7 Drawing Sheets

(A) PCOTH  (B) MICAL2-PV

U6 promoter-siRNA construct

EGFP   si1   si2   si3   si4

D4493

ACTB (B)

Colony formation assay in PC3 psiU6-si1    psiU6-si3    psiU6-si4 psiU6-siEGFP    psiU6-si2

GENES AND POLYPEPTIDES RELATING TO PROSTATE CANCERS

The present application is related to U.S. Ser. No. 60/414,873, filed Sep. 30, 2002, which is incorporated herein by reference.

TECHNICAL FIELD

The present invention relates to the field of biological science, more specifically to the field of cancer research. In particular, the present invention relates to novel polypeptides encoded by a novel gene A5736 (MICAL2-PV) and gene D4493 (PCOTH) relating to prostate cancer. Furthermore, the present invention relates to the novel gene A5736 (MICAL2-PV). The genes and polypeptides of the present invention can be used, for example, in the diagnosis of prostate cancer, as target molecules for developing drugs against the disease, and for attenuating cell growth of prostate cancer.

BACKGROUND ART

Prostate cancer is one of the most common cancers in male in Western countries (Gronberg, Lancet 361: 859-64 (2003)). Incidence of prostate cancer is steadily increasing in developed countries due to the prevalence of Western-style diet and increasing number of senior population. Early diagnosis through serum testing for prostate specific antigen (PSA) provides an opportunity for curative surgery and has significantly improved the prognosis of prostate cancer. However, up to 30% of patients treated with radical prostatectomy relapse cancer (Han et al., J Urol 166: 416-9 (2001)). Most relapsed or advanced cancers respond to androgen ablation therapy because the growth of prostate cancer is androgen-dependent in the initial stages. However, most of the patient treated by the therapy eventually progress to androgen-independent disease, at which point they are no longer responsive to the therapy. The most serious clinical problem of prostate cancer is that androgen-independent prostate cancer is unresponsive to any other therapies (Gronberg, Lancet 361: 859-64 (2003)). Thus, the establishment of new therapies other than androgen ablation therapy against prostate cancer is an urgent issue for the management of prostate cancer.

cDNA microarray technologies have enabled to obtain comprehensive profiles of gene expression in normal and malignant cells, and compare the gene expression in malignant and corresponding normal cells (Okabe et al., Cancer Res 61:2129-37 (2001); Kitahara et al., Cancer Res 61: 3544-9 (2001); Lin et al., Oncogene 21:4120-8 (2002); Hasegawa et al., Cancer Res 62:7012-7 (2002)). This approach enables to disclose the complex nature of cancer cells, and helps to understand the mechanism of carcinogenesis. Identification of genes that are deregulated in tumors can lead to more precise and accurate diagnosis of individual cancers, and to develop novel therapeutic targets (Bienz and Clevers, Cell 103:311-20 (2000)). To disclose mechanisms underlying tumors from a genome-wide point of view, and discover target molecules for diagnosis and development of novel therapeutic drugs, the present inventors have been analyzing the expression profiles of tumor cells using a cDNA microarray of 23040 genes (Okabe et al., Cancer Res 61:2129-37 (2001); Kitahara et al., Cancer Res 61:3544-9 (2001); Lin et al., Oncogene 21:4120-8 (2002); Hasegawa et al., Cancer Res 62:7012-7 (2002)).

Studies designed to reveal mechanisms of carcinogenesis have already facilitated identification of molecular targets for anti-tumor agents. For example, inhibitors of farnexyltransferase (FTIs) which were originally developed to inhibit the growth-signaling pathway related to Ras, whose activation depends on posttranslational farnesylation, has been effective in treating Ras-dependent tumors in animal models (He et al., Cell 99:33545 (1999)). Clinical trials on human using a combination or anti-cancer drugs and anti-HER2 monoclonal antibody, trastuzumab, have been conducted to antagonize the proto-oncogene receptor HER2/neu; and have been achieving improved clinical response and overall survival of breast-cancer patients (Lin et al., Cancer Res 61:6345-9 (2001)). A tyrosine kinase inhibitor, STI-571, which selectively inactivates bcr-abl fusion proteins, has been developed to treat chronic myelogenous leukemias wherein constitutive activation of ber-abl tyrosine kinase plays a crucial role in the transformation of leukocytes. Agents of these kinds are designed to suppress oncogenic activity of specific gene products (Fujita et al., Cancer Res 61:7722-6 (2001)). Therefore, gene products commonly up-regulated in cancerous cells may serve as potential targets for developing novel anti-cancer agents. In fact, novel drugs targeting abnormally expressed molecules that have causative effects on cancer growth and progression have been proven to be effective to certain types of cancers. Such drugs include Herceptin for breast cancer, Glivec (STI571) for CML and Iressa (ZD1839) for non-small cell lung cancer.

Several molecules have been known to be over-expressed in prostate cancer and are identified as therapeutic targets or markers of prostate cancer (Xu et al., Cancer Res 60: 6568-72 (2000); Luo et al., Cancer Res 62: 2220-6 (2002)). However, most of them are also highly expressed in other major organs. Thus, agents that target these molecules may be toxic to cancer cells but may also adversely affect normally growing cells of other organs.

It has been demonstrated that CD8+ cytotoxic T lymphocytes (CTLs) recognize epitope peptides derived from tumor-associated antigens (TAAs) presented on MHC Class I molecule, and lyse tumor cells. Since the discovery of MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994)). Some of the discovered TAAs are now in the stage of clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products which had been demonstrated to be specifically over-expressed in tumor cells, have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenbeg et al., Nature Med 4: 321-7 (1998); Mukhedji et al., Proc Natl Acad Sci USA 92: 8078-82 (1995); Hu et al., Cancer Res 56: 2479-83 (1996)), only limited number of candidate TAAs for the treatment of adenocarcinomas, including colorectal cancer, are available. TAAs abundantly expressed in cancer cells, and at the same time which expression is restricted to cancer cells would be promising candidates as immunotherapeutic targets. Further, identification of new TAAs inducing potent and specific anti-tumor immune responses is expected to encourage clinical use of peptide vaccination strategy in various types of cancer (Boon and can der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-5 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res 92: 762-7 (2001)). However, both of HLA-A24 and HLA-A0201 are one of the popular HLA alleles in Japanese, as well as Caucasian (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Histocompatibility Workshop and Conference Oxford University Press, Oxford, 1065 (1992); Williams et al., Tissue Antigen 49: 129 (1997)). Thus, antigenic peptides of cancers presented by these HLAs may be especially useful for the treatment of cancers among Japanese and Caucasian. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., Proc Natl Acad Sci USA 93: 4102-7 (1996)).

SUMMARY OF THE INVENTION

To disclose the mechanism of prostate cancer and identify novel diagnostic markers and/or drug targets for the treatment of these tumors, the present inventors analyzed the expression profiles of genes in prostate cancer using a genome-wide cDNA microarray combined with laser microbeam microdissection. From the pharmacological point of view, suppressing oncogenic signals is easier in practice than activating tumor-suppressive effects. Thus, the present inventors searched for genes that are over-expressed in prostate cancer cells.

As a result, two genes, PCOTH and MICAL2-PV, specifically over-expressed in prostate cancer cells were identified. Furthermore, reduction of PCOTH (prostate collagen triple helix) or MICAL2-PV (MICAL2 (Molecule Interacting with CasL 2) prostate cancer-variants) expression by transfection of small interfering RNAs (siRNAs) inhibited the growth of prostate cancer cells.

PCOTH encodes a 100-amino acid protein comprising a collagen triple helix repeat and its exogenous product was localized in the cell membrane. According to a Northern blot analysis, the expression of PCOTH was shown to be restricted to testis and prostate.

Furthermore, the expression of MICAL2-PV was also shown to be restricted to testis. The protein encoded by MICAL2-PV comprises a domain having homology to calponin domain, an actin-binding domain which is present in duplicate at the N-terminus of spectrin-like proteins including dystrophin and α-actinin. Thus, the protein encoded by MICAL2-PV is predicted to interact with actin or other microtubules. These domains cross-link actin filaments into bundles and networks. The other family member, MICAL1, is reported to be associated with vimentin (Suzuki et al., J Biol Chem 277: 14933-41 (2002)) and rab1 (Weide et al., Biochem Biophys Res Commun 306: 79-86 (2003)) that are major components of intermediated filaments and cytoskelton functioning as scaffold proteins connecting different components in the cell. MICAL2-PV protein is expected to be involved in the construction of cytoskelton and cell morphology in prostate cancer cells.

Many anticancer drugs are not only toxic to cancer cells but also for normally growing cells. However, agents suppressing the expression of MICAL2-PV or PCOTH may not adversely affect other organs due to the fact that normal expression of MICAL2-PV is restricted to testis and PCOTH is restricted to testis and prostate, and thus may be of great importance for treating or preventing prostate cancer.

Thus, the present invention provides isolated genes, MICAL2-PV and PCOTH, which serve as candidates of diagnostic markers for prostate cancer as well as promising potential targets for developing new strategies for diagnosis and effective anti-cancer agents. Furthermore, the present invention provides polypeptides encoded by these genes, as well as the production and the use of the same. More specifically, the present invention provides the following:

The present application provides novel human polypeptides, MICAL2-PV and PCOTH, or a functional equivalent thereof, which expressions are elevated in prostate cancer cells.

In a preferred embodiment, the MICAL2-PV polypeptide includes a putative 976 amino acid protein encoded by the open reading frame of SEQ ID NO: 3 or a putative 955 amino acid protein encoded by the open reading frame of SEQ IN NO: 5. The MICAL2-PV polypeptide preferably includes the amino acid sequence set forth in SEQ ID NO: 4 or 6. The present application also provides an isolated protein encoded from at least a portion of the MICAL2-PV polynucleotide sequence, or polynucleotide sequences at least 15% and more preferably at least 25% complementary to the sequence set forth in SEQ ID NO: 3 or 5.

On the other hand, in a preferred embodiment, the PCOTH polypeptide consists of a putative 100 amino acid sequence set forth in SEQ ID NO: 2 (GenBank® Accession No. AB 113650). PCOTH is encoded by the open reading frame of SEQ ID NO: 1 and comprises a collagen triple helix repeat (FIG. 1(C)). The present application also provides an isolated protein encoded from at least a portion of the PCOTH polynucleotide sequence, or polynucleotide sequences at least 30% and more preferably at least 40% complementary to the sequence set forth in SEQ ID NO: 1 (LOC221179(XP__167955)).

The present invention further provides a novel human gene MICAL2-PV whose expressions is markedly elevated in a great majority of prostate cancers as compared to corresponding non-cancerous prostate duct epithelium. The isolated MICAL2-PV gene includes a polynucleotide sequence as described in SEQ ID NO: 3 or 5. In particular, the MICAL2-PV cDNA includes 6805 nucleotides that contain an open reading frame of 2928 nucleotides (SEQ ID NO: 3) or 6742 nucleotides that contain an open reading frame of 2865 nucleotides (SEQ ID NO: 5). The present invention further encompasses polynucleotides which hybridize to and which are at least 30% and more preferably at least 40% complementary to the polynucleotide sequence set forth in SEQ ID NO: 3 or 5, to the extent that they encode a MICAL2-PV protein or a functional equivalent thereof. Examples of such polynucleotides are degenerates and allelic mutants of MICAL2-PV encoded by the sequence of SEQ ID NO: 3 or 5.

Furthermore, the present invention provides an isolated polynucleotide encoding the novel human protein PCOTH, whose expression is also markedly elevated in a great majority of prostate cancers as compared to corresponding non-cancerous prostate duct epithelium. The isolated polynucleotide encodes a polypeptide consisting of 100 amino acids described in SEQ ID NO: 2. More specifically, the isolated polynucleotide comprises the nucleotide sequence of SEQ ID NO: 1 from the 332 to the 631 nucleotide. The present invention further encompasses polynucleotides which hybridize to and which are at least 30%, and more preferably at least 40% complementary to the polynucleotide sequence set forth in SEQ ID NO: 1, to the extent that they encode a PCTOH protein or a functional equivalent thereof. Examples of such polynucleotides are degenerates and allelic mutants of SEQ ID NO: 1.

As used herein, an isolated gene is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion polypeptide.

Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1, 3 or 5. More preferably, the isolated nucleic acid molecule is at least 65%, 70%, 75%, 80%, 85%, 90%, 91%, 92%, 93%, 94%, 95%, 96%, 97%,98%, 99% or more, identical to the nucleotide sequence shown in SEQ ID NO: 1, 3 or 5. In the case of an isolated polynucleotide which is longer than or equivalent in length to the reference sequence, e.g., SEQ ID NO: 1, 3 or 5, the comparison is made with the full length of the reference sequence. Where the isolated polynucleotide is shorter than the reference sequence, e.g., shorter than SEQ ID NO: 1, 3 or 5, the comparison is made to segment of the reference sequence of the same length (excluding any loop required by the homology calculation).

The present invention also provides a method of producing a protein by transfecting or transforming a host cell with a polynucleotide sequence encoding the MICAL2-PV or PCOTH protein, and expressing the polynucleotide sequence. In addition, the present invention provides vectors comprising a nucleotide sequence encoding the MICAL2-PV or PCOTH protein, and host cells harboring a polynucleotide encoding the MICAL2-PV or PCOTH protein. Such vectors and host cells may be used for producing the MICAL2-PV or PCOTH protein.

An antibody that recognizes the MICAL2-PV protein is also provided by the present application. In part, an antisense polynucleotide (e.g., antisense DNA), ribozyme, and siRNA (small interfering RNA) of the MICAL2-PV or PCOTH gene is also provided.

The present invention further provides a method for diagnosis of prostate cancer which includes the step of determining an expression level of the gene in a biological sample from a subject, comparing the expression level of MICAL2-PV or PCOTH gene with that in a normal sample, and defining that a high expression level of the MICAL2-PV or PCOTH gene in the sample indicates that the subject suffers from or is at risk of developing prostate cancer.

Further, a method of screening for a compound for treating or preventing prostate cancer is provided by the present invention. The method includes contacting the MICAL2-PV or PCOTH polypeptide with test compounds, and selecting test compounds that bind to or that alter the biological activity of the MICAL2-PV or PCOTH polypeptide.

The present invention further provides a method of screening for a compound for treating or preventing prostate cancer, wherein the method includes contacting a test compound with a cell expressing the MICAL2-PV or PCOTH polypeptide or introduced with a vector comprising the transcriptional regulatory region of MICAL2-PV or PCOTH upstream of a reporter gene, and selecting the test compound that suppresses the expression level of the MICAL2-PV or PCOTH polypeptide.

Alternatively, the present invention provides a method of screening for a compound for treating or preventing prostate cancer, wherein the method includes contacting MICAL2-PV and actin in the presence of a test compound, and selecting the test compound that inhibits the binding of MICAL2-PV and actin.

The present application also provides a pharmaceutical composition for treating or preventing prostate cancer. The pharmaceutical composition may be, for example, an anti-cancer agent. The pharmaceutical composition can be described as at least a portion of the antisense S-oligonucleotides, siRNA or ribozyme against the MICAL2-PV or PCOTH polynucleotide sequence shown and described in SEQ ID NOs: 3 and 5, or 1, respectively. A suitable siRNA targets a sequence selected from the group of SEQ ID NOs: 23 and 27. The target sequence of MICAL2-PV siRNA comprises the nucleotide sequence of SEQ ID NO: 27, and that of PCOTH siRNA comprises the nucleotide sequence of SEQ ID NO: 23. Both may be preferably selected as targets for treating or preventing prostate cancer according to the present invention. The pharmaceutical compositions may be also those comprising the compounds selected by the present methods of screening for compounds for treating or preventing cell proliferative diseases such as prostate cancer.

The course of action of the pharmaceutical composition is desirably to inhibit growth of the cancerous cells such as prostate cancer cells. The pharmaceutical composition may be applied to mammals including humans and domesticated mammals.

The present invention further provides methods for treating or preventing prostate cancer using the pharmaceutical composition provided by the present invention.

In addition, the present invention provides method for treating or preventing cancer, which method comprises the step of administering the MICAL2-PV or PCOTH polypeptide. It is expected that anti tumor immunity be induced by the administration of the MICAL2-PV or PCOTH polypeptide. Thus, the present invention also provides method for inducing anti tumor immunity, which method comprises the step of administering the MICAL2-PV or PCOTH polypeptide, as well as pharmaceutical composition for treating or preventing cancer comprising the MICAL2-PV or PCOTH polypeptide.

It is to be understood that both the foregoing summary of the invention and the following detailed description are of a preferred embodiment, and not restrictive of the invention or other alternate embodiments of the invention.

DETAILED DESCRIPTION OF THE INVENTION

Figure 1:
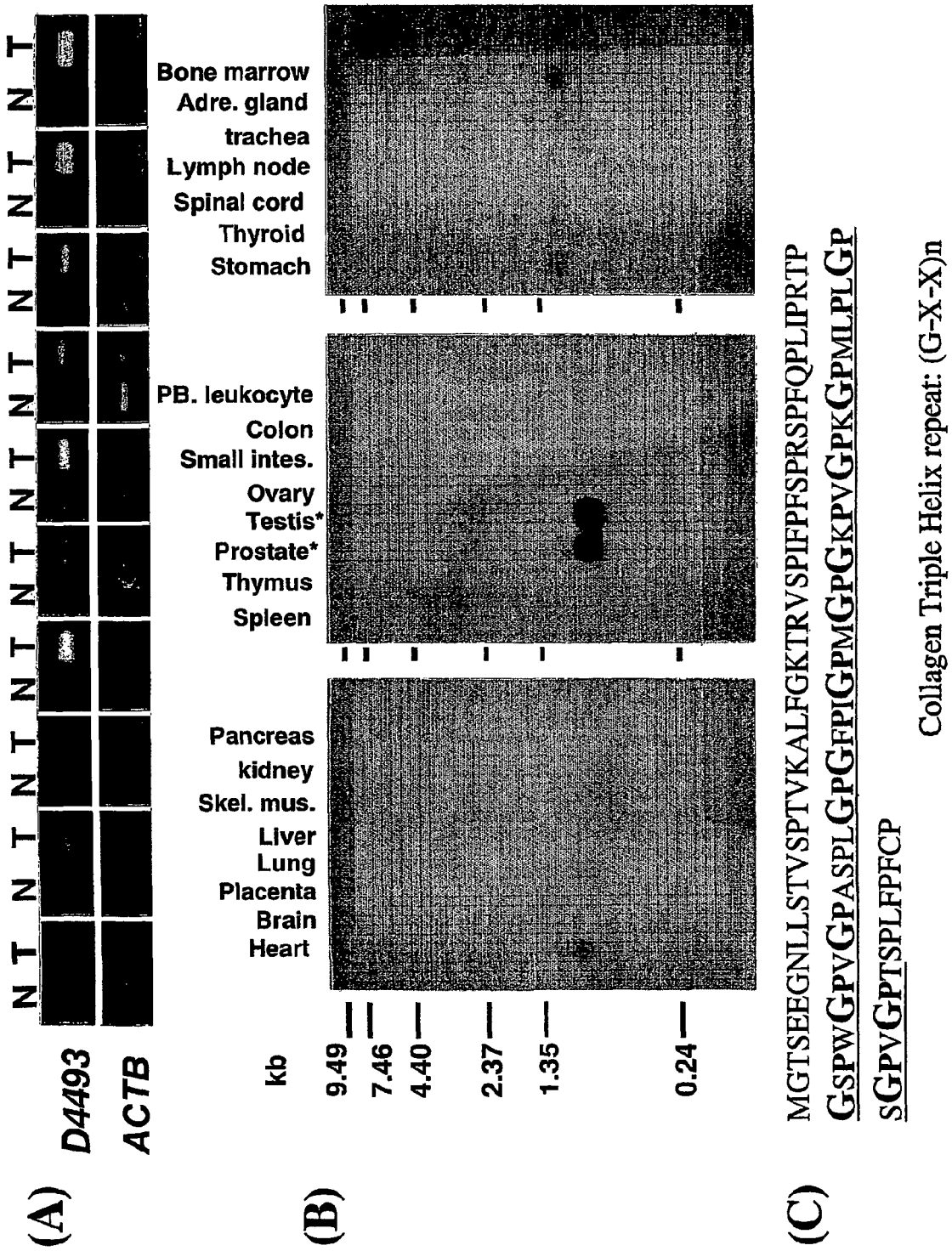
FIG. 1(A) depicts photographs showing the result of validation of over-expression of D4493 (PCOTH) in prostate cancer cells by RT-PCR. The microdissected normal prostate duct epithelial cells (N) and prostate cancer cells (T) from the same individual were compared by semiquantitative RT-PCR. ACTB was used for normalization of the results. (B) depicts photographs showing the result of Northern blot analysis of normal human multiple tissues. High and localized expression in testis and prostate and minor expression in heart and bone marrow were detected. (C) depicts the amino acid sequence of D4493 (PCOTH) product (SEQ ID NO:2). The product consists of 100 amino acids and has collagen triple helix repeats which is characterized by the G-X-X motif repeat. G is glycine and X is preferably proline.

The words "a", "an" and "the" as used herein mean "at least one" unless otherwise specifically indicated.

To disclose the mechanism of prostate cancer and identify novel diagnostic markers and/or drug targets for the treatment of these tumors, the present inventors analyzed the expression profiles of genes in prostate cancer using a genome-wide cDNA microarray combined with laser microbeam microdissection. As a result, two genes, PCOTH and MICAL2-PV, specifically over-expressed in prostate cancer cells were identified. Furthermore, suppression of the expression of PCOTH or MICAL2-PV gene with small interfering RNAs (siRNAs) resulted in a significant growth-inhibition of cancerous cells. These findings suggest that PCOTH and MICAL2-PV render oncogenic activities to cancer cells, and that inhibition of the activity of these proteins could be a promising strategy for the treatment and prevention of proliferative diseases such as prostate cancers.

MICAL2-PV

According to the present invention, two genes with a similar sequence were identified and suggested to encode variants of MICAL2 that consist of 1124 amino acid residues. The expression of the two genes was markedly elevated in prostate cancer compared to corresponding non-cancerous tissues. The coding region of the 3' terminus of the identified variants differed from that of MICAL2. Thus, these two novel human genes were collectively dubbed "MICAL2 prostate cancer-variants (MICAL2-PV)". The cDNA of the longer variant consists of 6805 nucleotides containing an open reading frame of 2928 nucleotides (SEQ ID NO: 3) and the shorter variant consists of 6742 nucleotides containing an open reading frame of 2865 nucleotides (SEQ ID NO: 5). These open reading frames encode a putative 976 amino acid-protein and a putative 955 amino acid-protein, respectively. The protein encoded by MICAL2-PV comprises a domain having homology to calponin domain, an actin-binding domain which is present in duplicate at the N-terminus of spectrin-like proteins including dystrophin and α-actinin. Therefore, the protein encoded by MICAL2-PV is predicted to interact with actin or other microtubules. These domains cross-link actin filaments into bundles and networks.

Thus, the present invention provides substantially pure polypeptides encoded by these genes including polypeptides comprising the amino acid sequence of SEQ ID NO: 4 or 6, as well as functional equivalents thereof, to the extent that they encode a MICAL2-PV protein. Examples of polypeptides functionally equivalent to MICAL2-PV include, for example, homologous proteins of other organisms corresponding to the human MICAL2-PV protein, as well as mutants of human MICAL2-PV proteins.

In the present invention, the term "functionally equivalent" means that the subject polypeptide has the activity to promote cell proliferation like the MICAL2-PV protein and to confer oncogenic activity to cancer cells. Whether the subject polypeptide has a cell proliferation activity or not can be judged by introducing the DNA encoding the subject polypeptide into a cell expressing the respective polypeptide and detecting promotion of proliferation of the cells or increase in colony forming activity. Such cells include, for example, LNCaP, PC3 and DU145. Alternatively, whether the subject polypeptide is functionally equivalent to MICAL2-PV may be judged by detecting its binding ability to actin.

Methods for preparing polypeptides functionally equivalent to a given protein are well known by a person skilled in the art and include known methods of introducing mutations into the protein. For example, one skilled in the art can prepare polypeptides functionally equivalent to the human MICAL2-PV protein by introducing an appropriate mutation in the amino acid sequence of either of these proteins by site-directed mutagenesis (Hashimoto-Gotoh et al., Gene 152:271-5 (1995); Zoller and Smith, Methods Enzymol 100: 468-500 (1983); Kramer et al., Nucleic Acids Res. 12:9441-9456 (1984); Kramer and Fritz, Methods Enzymol 154: 350-67 (1987); Kunkel, Proc Natl Acad Sci USA 82: 488-92 (1985); Kunkel, Methods Enzymol 85: 2763-6 (1988)). Amino acid mutations can occur in nature, too. The polypeptide of the present invention includes those proteins having the amino acid sequences of the human MICAL2-PV protein in which one or more amino acids are mutated, provided the resulting mutated polypeptides are functionally equivalent to the human MICAL2-PV protein. The number of amino acids to be mutated in such a mutant is generally 10 amino acids or less, preferably 6 amino acids or less, and more preferably 3 amino acids or less.

Mutated or modified proteins, proteins having amino acid sequences modified by substituting, deleting, inserting and/or adding one or more amino acid residues of a certain amino acid sequence, have been known to retain the original biological activity (Mark et al., Proc Natl Acad Sci USA 81: 5662-6 (1984); Zoller and Smith, Nucleic Acids Res 10:6487-500 (1982); Dalbadie-McFarland et al., Proc Natl Acad Sci USA 79: 6409-13 (1982)).

The amino acid residue to be mutated is preferably mutated into a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, C H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

An example of a polypeptide to which one or more amino acids residues are added to the amino acid sequence of human MICAL2-PV protein is a fusion protein containing the human MICAL2-PV protein. Fusion proteins are, fusions of the human MICAL2-PV protein and other peptides or proteins, and are included in the present invention. Fusion proteins can be made by techniques well known to a person skilled in the art, such as by linking the DNA encoding the human MICAL2-PV protein of the invention with DNA encoding other peptides or proteins, so that the frames match, inserting the fusion DNA into an expression vector and expressing it in a host. There is no restriction as to the peptides or proteins fused to the protein of the present invention.

Known peptides that can be used as peptides that are fused to the protein of the present invention include, for example, FLAG (Hopp et al., Biotechnology 6: 1204-10 (1988)), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment and the like. Examples of proteins that may be fused to a protein of the invention include GST (glutathione-S-transferase), Influenza agglutinin (HA), immunoglobulin constant region, β-galactosidase, MBP (maltose-binding protein) and such.

Fusion proteins can be prepared by fusing commercially available DNA, encoding the fusion peptides or proteins discussed above, with the DNA encoding the polypeptide of the present invention and expressing the fused DNA prepared.

An alternative method known in the art to isolate functionally equivalent polypeptides is, for example, the method using a hybridization technique (Sambrook et al., Molecular Cloning 2nd ed. 9.47-9.58, Cold Spring Harbor Lab. Press (1989)). One skilled in the art can readily isolate a DNA having high homology with a whole or part of the DNA sequence encoding the human MICAL2-PV protein (i.e., SEQ ID NO: 3 or 5), and isolate functionally equivalent polypeptides to the human MICAL2-PV protein from the isolated DNA. The polypeptides of the present invention include those that are encoded by DNA that hybridize with a whole or part of the DNA sequence encoding the human MICAL2-PV protein and are functionally equivalent to the human MICAL2-PV protein. These polypeptides include mammal homologues corresponding to the protein derived from human (for example, a polypeptide encoded by a monkey, rat, rabbit and bovine gene). In isolating a cDNA highly homologous to the DNA encoding the human MICAL2-PV protein from animals, it is particularly preferable to use tissues from testis.

The condition of hybridization for isolating a DNA encoding a polypeptide functionally equivalent to the human MICAL2-PV protein can be routinely selected by a person skilled in the art. For example, hybridization may be performed by conducting prehybridization at 68° C. for 30 min or longer using "Rapid-hyb buffer" (Amersham LIFE SCIENCE), adding a labeled probe, and warming at 68° C. for 1 hour or longer. The following washing step can be conducted, for example, in a low stringent condition. A low stringent condition is, for example, 42° C., 2×SSC, 0.1% SDS, or preferably 50° C., 2×SSC, 0.1% SDS. More preferably, high stringent conditions are used. A high stringent condition is, for example, washing 3 times in 2×SSC, 0.01% SDS at room temperature for 20 min, then washing 3 times in 1×SSC, 0.1% SDS at 37° C. for 20 min, and washing twice in 1×SSC, 0.1% SDS at 50° C. for 20 min. However, several factors, such as temperature and salt concentration, can influence the stringency of hybridization and one skilled in the art can suitably select the factors to achieve the requisite stringency.

In place of hybridization, a gene amplification method, for example, the polymerase chain reaction (PCR) method, can be utilized to isolate a DNA encoding a polypeptide functionally equivalent to the human MICAL2-PV protein, using a primer synthesized based on the sequence information of the protein encoding DNA (SEQ ID NO: 3 or 5).

Polypeptides that are functionally equivalent to the human MICAL2-PV protein encoded by the DNA isolated through the above hybridization techniques or gene so amplification techniques normally have a high homology to the amino acid sequence of the human MICAL2-PV protein. "High homology" typically refers to a homology of 40% or higher, preferably 60% or higher, more preferably 80% or higher, even more preferably 95% or higher. The homology of a polypeptide can be determined by following the algorithm in "Wilbur and Lipman, Proc Natl Acad Sci USA 80: 726-30 (1983)". A polypeptide of the present invention may have variations in amino acid sequence, molecular weight, isoelectric point, the presence or absence of sugar chains, or form, depending on the cell or host used to produce it or the purification method utilized. Nevertheless, so long as it has a function equivalent to that of the human MICAL2-PV protein of the present invention, it is within the scope of the present invention.

The polypeptides of the present invention can be prepared as recombinant proteins or natural proteins, by methods well known to those skilled in the art. A recombinant protein can be prepared by inserting a DNA, which encodes the polypeptide of the present invention (for example, the DNA comprising the nucleotide sequence of SEQ ID NO: 3 or 5), into an appropriate expression vector, introducing the vector into an appropriate host cell, obtaining the extract, and purifying the polypeptide by subjecting the extract to chromatography, e.g., ion exchange chromatography, reverse phase chromatography, gel filtration or affinity chromatography utilizing a column to which antibodies against the protein of the present invention is fixed or by combining more than one of aforementioned columns.

Also when the polypeptide of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column. Alternatively, when the polypeptide of the present invention is expressed as a protein tagged with c-myc, multiple histidines or FLAG, it can be detected and purified using antibodies to c-myc, His or FLAG respectively.

After purifying the fusion protein, it is also possible to exclude regions other than the objective polypeptide by cutting with thrombin or factor-Xa as required.

A natural protein can be isolated by methods known to a person skilled in the art, for example, by contacting the affinity column, in which antibodies binding to the MICAL2-PV protein described below are bound, with the extract of tissues or cells expressing the polypeptide of the present invention. The antibodies can be polyclonal antibodies or monoclonal antibodies.

The present invention also encompasses partial peptides of the polypeptide of the present invention. The partial peptide has an amino acid sequence specific to the polypeptide of the present invention and consists of at least 7 amino acids, preferably 8 amino acids or more, and more preferably 9 amino acids or more. The partial peptide can be used, for example, for preparing antibodies against the polypeptide of the present invention, screening for a compound that binds to the polypeptide of the present invention, and screening for accelerators or inhibitors of the polypeptide of the present invention.

A partial peptide of the invention can be produced by genetic engineering, by known methods of peptide synthesis or by digesting the polypeptide of the invention with an appropriate peptidase. For peptide synthesis, for example, solid phase synthesis or liquid phase synthesis may be used.

The present invention further provides polynucleotides that encode such MICAL2-PV polypeptides described above. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention include a DNA comprising a given nucleotide sequences as well as its degenerate sequences, so long as the resulting DNA encodes a polypeptide of the present invention.

The polynucleotide of the present invention can be prepared by methods known to a person skilled in the art. For example, the polynucleotide of the present invention can be prepared by: preparing a cDNA library from cells which express the polypeptide of the present invention, and conducting hybridization using a partial sequence of the DNA of the present invention (for example, SEQ ID NO: 3 or 5) as a probe. A cDNA library can be prepared, for example, by the method described in Sambrook et al., Molecular Cloning, Cold Spring Harbor Laboratory Press (1989); alternatively, commercially available cDNA libraries may be used. A cDNA library can be also prepared by: extracting RNAs from cells expressing the polypeptide of the present invention, synthesizing oligo DNAs based on the sequence of the DNA of the present invention (for example, SEQ ID NO: 3 or 5), conducting PCR using the oligo DNAs as primers, and amplifying cDNAs encoding the protein of the present invention.

In addition, by sequencing the nucleotides of the obtained cDNA, the translation region encoded by the cDNA can be routinely determined, and the amino acid sequence of the polypeptide of the present invention can be easily obtained. Moreover, by screening the genomic DNA library using the obtained cDNA or parts thereof as a probe, the genomic DNA can be isolated.

More specifically, mRNAs may first be prepared from a cell, tissue or organ (e.g., testis) in which the object polypeptide of the invention is expressed. Known methods can be used to isolate mRNAs; for instance, total RNA may be prepared by guanidine ultracentrifugation (Chirgwin et al., Biochemistry 18:5294-9 (1979)) or AGPC method (Chomczynski and Sacchi, Anal Biochem 162:156-9 (1987)). In addition, mRNA may be purified from total RNA using mRNA Purification Kit (Pharmacia) and such. Alternatively, mRNA may be directly purified by QuickPrep mRNA Purification Kit (Pharmacia).

The obtained mRNA is used to synthesize cDNA using reverse transcriptase. cDNA may be synthesized using a commercially available kit, such as the AMV Reverse Transcriptase First-strand cDNA Synthesis Kit (Seikagaku Kogyo). Alternatively, cDNA may be synthesized and amplified following the 5'-RACE method (Frohman et al., Proc Natl Acad Sci USA 85: 8998-9002 (1988); Belyavsky et al., Nucleic Acids Res 17: 2919-32 (1989)), which uses a primer and such, described herein, the 5'-Ampli FINDER RACE Kit (Clontech), and polymerase chain reaction (PCR).

A desired DNA fragment is prepared from the PCR products and ligated with a vector DNA, The recombinant vectors are used to transform *E. coli* and such, and a desired recombinant vector is prepared from a selected colony. The nucleotide sequence of the desired DNA can be verified by conventional methods, such as dideoxynucleotide chain termination.

The nucleotide sequence of a polynucleotide of the invention may be designed to be expressed more efficiently by taking into account the frequency of codon usage in the host to be used for expression (Grantham et al., Nucleic Acids Res 9: 43-74 (1981)). The sequence of the polynucleotide of the present invention may be altered by a commercially available kit or a conventional method. For instance, the sequence may be altered by digestion with restriction enzymes, insertion of a synthetic oligonucleotide or an appropriate polynucleotide fragment, addition of a linker, or insertion of the initiation codon (ATG) and/or the stop codon (TAA, TGA or TAG).

Specifically, the polynucleotide of the present invention encompasses the DNA comprising the nucleotide sequence of SEQ ID NO: 3 or 5.

Furthermore, the present invention provides a polynucleotide that hybridizes under stringent conditions with a polynucleotide having a nucleotide sequence of SEQ ID NO: 3 or 5, and encodes a polypeptide functionally equivalent to the MICAL2-PV protein of the invention described above. One skilled in the art may appropriately choose stringent conditions. For example, low stringent condition can be used. More preferably, high stringent condition can be used. These conditions are the same as that described above. The hybridizing DNA above is preferably a cDNA or a chromosomal DNA.

The present invention also provides a polynucleotide which is complementary to the polynucleotide encoding human MICAL2-PV protein (SEQ ID NO: 3 or 5) or the complementary strand thereof, and which comprises at least 15 nucleotides. The polynucleotide of the present invention is preferably a polynucleotide which specifically hybridizes with the DNA encoding the MICAL2-PV polypeptide of the present invention. The term "specifically hybridize" as used herein, means that cross-hybridization does not occur significantly with DNA encoding other proteins, under the usual hybridizing conditions, preferably under stringent hybridizing conditions. Such polynucleotides include, probes, primers, nucleotides and nucleotide derivatives (for example, antisense oligonucleotides and ribozymes), which specifically hybridize with DNA encoding the polypeptide of the invention or its complementary strand. Moreover, such polynucleotide can be utilized for the preparation of DNA chip.

PCOTH

According to the present invention another gene, PCOTH, was also identified to be specifically over-expressed in prostate cancer cells compared to corresponding non-cancerous tissues. The identified gene was identical with LOC221179 (XP$_{13}$ 167955). However, the PCOTH gene was revealed to encode a 100-amino acid protein set forth in SEQ ID NO: 2 (GenBank® Accession No. AB113650) encoded by the open reading frame consisting of 300 nucleotides shown in SEQ ID NO: 1 which differed from that known for LOC221179 (XP_167955). PCOTH was shown to comprise a collagen triple helix repeat and its exogenous product was localized in the cell membrane (FIG. 1). Therefore, the gene was dubbed "prostate collagen triple helix".

Thus, the present invention provides substantially pure polypeptides encoded by the gene including polypeptides consisting of the amino acid sequence of SEQ ID NO: 2, as well as functional equivalents thereof, to the extent that they encode a PCOTH protein and such functional equivalents are expected to be shorter than the whole amino acid sequence encoded by the known LOC221179 (XP_167955). Examples of polypeptides functionally equivalent to PCOTH include, for example, homologous proteins of other organisms corresponding to the human PCOTH protein, as well as mutants of human PCOTH proteins. Preferable mutants of PCOTH protein includes those consisting of the amino acid sequence of SEQ ID NO: 2 in which one or more amino acids are substituted and/or deleted.

In the present invention, the term "functionally equivalent" means that the subject polypeptide has the activity to promote cell proliferation like the PCOTH protein and to confer oncogenic activity to cancer cells. Whether the subject polypeptide has a cell proliferation activity or not can be judged by introducing the DNA encoding the subject polypeptide into a cell expressing the respective polypeptide and detecting promotion of proliferation of the cells or increase in colony forming activity. Such cells include, for example, LNCaP, PC3 and DU145.

The same methods as those described in the item of "MICAL2-PV" above can be employed for preparing the PCOTH protein and functional equivalents thereof using sequence information described in SEQ ID NOs: 1 and 2.

The present invention further provides polynucleotides that encode such PCOTH polypeptides described above. The polynucleotides of the present invention can be used for the in vivo or in vitro production of the polypeptide of the present invention as described above, or can be applied to gene therapy for diseases attributed to genetic abnormality in the gene encoding the protein of the present invention. Any form of the polynucleotide of the present invention can be used so long as it encodes the polypeptide of the present invention, including mRNA, RNA, cDNA, genomic DNA, chemically synthesized polynucleotides. The polynucleotide of the present invention include a DNA comprising a given nucleotide sequences as well as its degenerate sequences, so long as the resulting DNA encodes a PCOTH polypeptide of the present invention. Such polynucleotides can also be prepared according to method similar to those described under the item of "MICAL2-PV" using sequence information described in SEQ ID NOs: 1 and 2.

In contrast to MICAL2-PV, normal expression of PCOTH was detected in testis and also prostate. Thus, for preparing PCOTH or functionally equivalents thereof, or the mRNA of PCOTH, in addition to testis tissues, one can use tissues from prostate.

Vectors and Host Cells

The present invention also provides a vector and host cell into which a polynucleotide of the present invention is introduced. A vector of the present invention is useful to keep a polynucleotide, especially a DNA, of the present invention in host cell, to express the polypeptide of the present invention, or to administer the polynucleotide of the present invention for gene therapy.

When E. coli is a host cell and the vector is amplified and produced in a large amount in E. coli (e.g., JM109, DH5α, HB101 or XL1Blue), the vector should have "ori" to be amplified in E. coli and a marker gene for selecting transformed E. coli (e.g., a drug-resistance gene selected by a: drug such as ampicillin, tetracycline, kanamycin, chloramphenicol or the like). For example, M13-series vectors, pUC-series vectors, pBR322, pBluescript, pCR-Script, etc. can be used. In addition, pGEM-T, pDIRECT and pT7 can also be used for subcloning and extracting eDNA as well as the vectors described above. When a vector is used to produce the protein of the present invention, an expression vector is especially useful. For example, an expression vector to be expressed in E. coli should have the above characteristics to be amplified in E. coli. When E. coli, such as JM109, DH5α, HB101 or XL1 Blue, are used as a host cell, the vector should have a promoter, for example, lacZ promoter (Ward et al., Nature 341: 544-6 (1989); FASEB J 6:2422-7 (1992)), araB promoter (Better et al., Science 240:1041-3 (1988)), T7 promoter or the like, that can efficiently express the desired gene in E. coli. In that respect, pGEX-5X-1 (Pharmacia), "QIAexpress™ system" (Qiagen), pEGFP and pET (in this case, the host is preferably BL21 which expresses T7 RNA polymerase), for example, can be used instead of the above vectors. Additionally, the vector may also contain a signal sequence for polypeptide secretion. An exemplary signal sequence that directs the polypeptide to be secreted to the periplasm of the E. coli is the pelB signal sequence (Lei et al., J Bacteriol 169:4379 (1987)). Means for introducing of the vectors into the target host cells include, for example, the calcium chloride method, and the electroporation method.

In addition to *E. coli,* for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vector derived from yeast (e.g., "Pichia Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells, such as CHO, COS or NIH3T3 cells, the vector should have a promoter necessary for expression in such cells, for example, the SV40 promoter (Mulligan et al., Nature 277:,108 (1979)), the MMLV-LTR promoter, the EF1α promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

Producing Polypeptides

In addition, the present invention provides methods for producing a polypeptide of the present invention. The polypeptides may be prepared by culturing a host cell which harbors a expression vector comprising a gene encoding the polypeptide. According to needs, methods may be used to express a gene stably and, at the same time, to amplify the copy number of the gene in cells. For example, a vector comprising the complementary DHFR gene (e.g., pCHO I) may be introduced into CHO cells in which the nucleic acid synthesizing pathway is deleted, and then amplified by methotrexate (MTX). Furthermore, in case of transient expression of a gene, the method wherein a vector comprising a replication origin of SV40 (pcD, etc.) is transformed into COS cells comprising the SV40 T antigen expressing gene on the chromosome can be used.

A polypeptide of the present invention obtained as above may be isolated from inside or outside (such as medium) of host cells and purified as a substantially pure homogeneous polypeptide. The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis. The method for polypeptide isolation and purification is not limited to any specific method; in fact, any standard method may be used.

For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide.

Examples of chromatography include, for example, affinity chromatography, ion-exchange chromatography, hydrophobic chromatography, gel filtration, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies may be performed by liquid chromatography, such as HPLC and FPLC. Thus, the present invention provides for highly purified-polypeptides prepared by the above methods.

A polypeptide of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, glucosidase and so on.

Antibodies

The present invention provides an antibody that binds to the polypeptide of the invention. The antibody of the invention can be used in any form, such as monoclonal or polyclonal antibodies, and includes antiserum obtained by immunizing an animal such as a rabbit with the polypeptide of the invention, all classes of polyclonal and monoclonal antibodies, human antibodies and humanized antibodies produced by genetic recombination.

A polypeptide of the invention used as an antigen to obtain an antibody may be derived from any animal species, but preferably is derived from a mammal such as a human, mouse, or rat, more preferably from a human. A human-derived polypeptide may be obtained from the nucleotide or amino acid sequences disclosed herein. According to the present invention, the polypeptide to be used as an immunization antigen may be a complete protein or a partial peptide of the protein. A partial peptide may comprise, for example, the amino (N)-terminal or carboxy (C)-terminal fragment of a polypeptide of the present invention.

Herein, an antibody is defined as a protein that reacts with either the full length or a fragment of a polypeptide of the present invention.

A gene encoding a polypeptide of the invention or its fragment may be inserted into a known expression vector, which is then used to transform a host cell as described herein. The desired polypeptide or its fragment may be recovered from the outside or inside of host cells by any standard method, and may subsequently be used as an antigen. Alternatively, whole cells expressing the polypeptide or their lysates or a chemically synthesized polypeptide may be used as the antigen.

Any mammalian animal may be immunized with the antigen, but preferably the compatibility with parental cells used for cell fusion is taken into account. In general, animals of Rodentia, Lagomorpha or Primates are used. Animals of Rodentia include, for example, mouse, rat and hamster. Animals of Lagomorpha include, for example, rabbit Animals of Primates include, for example, a monkey of Catarrhini (old world monkey) such as *Macaca fascicularis,* rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined by a standard method for an increase in the amount of desired antibodies.

Polyclonal antibodies against the polypeptides of the present invention may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the polypeptide of the present invention using, for example, an affinity column coupled with the polypeptide of the present invention, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al. (Galfre and Milstein, Methods Enzymol 73: 3-46 (1981)).

Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with a polypeptide, polypeptide expressing cells or their lysates in vitro. Then, the immunized lymphocytes are fused with human-derived myeloma cells that are capable of indefinitely dividing, such as U266, to yield a hybridoma producing a desired human antibody that is able to bind to the polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography or an affinity column to which the polypeptide of the present invention is coupled. The antibody of the present invention can be used not only for purification and detection of the polypeptide of the present invention, but also as a candidate for agonists and antagonists of the polypeptide of the present invention. In addition, this antibody can be applied to the antibody treatment for diseases related to the polypeptide of the present invention. When the obtained antibody is to be administered to the human body (antibody treatment), a human antibody or-a humanized antibody is preferable for reducing immunogenicity.

For example, transgenic animals having a repertory of human antibody genes may be immunized with an antigen selected from a polypeptide, polypeptide expressing cells or their lysates. Antibody producing cells are then collected from the animals and fused with myeloma cells to obtain hybridoma, from which human antibodies against the polypeptide can be prepared (see WO92-03918, WO93-2227, WO94-02602, WO94-25585, WO96-33735 and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck and Larrick, Therapeutic Monoclonal Antibodies, published in the United Kingdom by MacMillan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the polypeptides of the invention. For instance, the antibody fragment may be Fab, $F(ab')_2$, Fv or single chain Fv (scFv), in which Fv fragments from H and L chains are ligated by an appropriate linker (Huston et al., Proc Natl Acad Sci USA 85: 5879-83 (1988)). More specifically, an antibody fragment may be generated by treating an antibody with an enzyme, such as papain or pepsin. Alternatively, a gene encoding the antibody fragment may be constructed, inserted into an expression vector and expressed in an appropriate host cell (see, for example, Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

An antibody may be modified by conjugation with a variety of molecules, such as polyethylene glycol (PEG). The present invention provides for such modified antibodies. The modified antibody can be obtained by chemically modifying an antibody. These modification methods are conventional in the field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody and the constant region. Such antibodies can be prepared according to known technology.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis and isoelectric focusing (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS and Sepharose F. F. (Pharmacia).

Exemplary chromatography, with the exception of affinity includes, for example, ion-exchange chromatography, hydrophobic chromatography, gel filtration, reverse-phase chromatography, adsorption chromatography and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

For example, measurement of absorbance, enzyme-linked immunosorbent assay (ELISA), enzyme immunoassay (EIA), radioimmunoassay (RIA) and/or immunofluorescence maybe used to measure the antigen binding activity of the antibody of the invention. In ELISA, the antibody of the present invention is immobilized on a plate, a polypeptide of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the polypeptide, such as a C-terminal or N-terminal fragment, may be used as the antigen to evaluate the binding activity of the antibody. BIAcore™ (Pharmacia) may be used to evaluate the activity of the antibody according to the present invention.

The above methods allow for the detection or measurement of the polypeptide of the invention, by exposing the antibody of the invention to a sample assumed to contain the polypeptide of the invention, and detecting or measuring the immune complex formed by the antibody and the polypeptide.

Because the method of detection or measurement of the polypeptide according to the invention can specifically detect or measure a polypeptide, the method may be useful in a variety of experiments in which the polypeptide is used.

Antisense Polynucleotides, Small Interfering RNAs and Ribozymes

The present invention includes an antisense oligonucleotide that hybridizes with any site within the nucleotide sequence of SEQ ID NO: 1, 3 or 5. This antisense oligonucleotide is preferably against at least 15 continuous nucleotides of the nucleotide sequence of SEQ ID NO: 1, 3 or 5. The above-mentioned antisense oligonucleotide, which contains an initiation codon in the above-mentioned at least 15 continuous nucleotides, is even more preferred.

Derivatives or modified products of antisense oligonucleotides can also be used as antisense oligonucleotides. Examples of such modified products include lower alkyl phosphonate modifications such as methyl-phosphonate-type or ethyl-phosphonate-type, phosphorothioate modifications and phosphoroamidate modifications.

The term "antisense oligonucleotides" as used herein means, not only those in which the nucleotides corresponding to those constituting a specified region of a DNA or mRNA are entirely complementary, but also those having a mismatch of one or more nucleotides, as long as the DNA or mRNA and the antisense oligonucleotide can specifically hybridize with the nucleotide sequence of SEQ ID NO: 1, 3 or 5.

Such polynucleotides are contained as those having, in the "at least 15 continuous nucleotide sequence region", a homology of at least 70% or higher, preferably at 80% or higher, more preferably 90% or higher, even more preferably 95% or higher. The algorithm stated herein can be used to determine the homology. Algorithms known in the art can be used to determine the homology. Furthermore, derivatives or modified products of the antisense-oligonucleotides can also be used as antisense-oligonucleotides in the present invention. Examples of such modified products include lower alkyl phosphonate modifications such as methyl-phosphonate-type or ethyl-phosphonate-type, phosphorothioate modifications and phosphoroamidate modifications.

Such antisense polynucleotides are useful as probes for the isolation or detection of DNA encoding the polypeptide of the invention or as a primer used for amplifications.

The antisense oligonucleotide derivatives of the present invention act upon cells producing the polypeptide of the invention by binding to the DNA or mRNA encoding the polypeptide, inhibiting its transcription or translation, promoting the degradation of the mRNA and inhibiting the expression of the polypeptide of the invention, thereby resulting in the inhibition of the polypeptide's function.

The present invention also includes small interfering RNAs (siRNA) comprising a combination of a sense strand nucleic acid and an antisense strand nucleic acid of the nucleotide sequence of SEQ ID NO: 1, 3 or 5. More specifically, such siRNA for suppressing the expression of MICAL2-PV include those that target the nucleotide sequence of SEQ ID NO: 27. Alternatively, siRNA for suppressing the expression of PCOTH include those that target the nucleotide sequence of SEQ ID NO: 23.

The term "siRNA" refers to a double stranded RNA molecule which prevents translation of a target mRNA. Standard techniques are used for introducing siRNA into cells, including those wherein DNA is used as the template to transcribe RNA. The siRNA comprises a sense nucleic acid sequence and an anti-sense nucleic acid sequence of the polynucleotide encoding human MICAL2-PV or PCOTH protein (SEQ ID NO: 1, 3 or 5). The siRNA is constructed such that a single transcript (double stranded RNA) has both the sense and complementary antisense sequences from the target gene, e.g., a hairpin.

The nucleotide sequence of siRNAs may be designed using an siRNA design 20 computer program available from the Ambion website on the world wide web. Nucleotide sequences for tile siRNA are selected by the computer program based on the following protocol:

Selection of siRNA Target Sites:

1. Beginning with the AUG start codon of the object transcript, scan downstream for AA dinucleotide sequences. Record the occurrence of each AA and the 3' adjacent 19 nucleotides as potential siRNA target sites. Tuschl, et al. recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with the binding of the siRNA endonuclease complex.

2. Compare the potential target sites to the human genome database and eliminate from consideration any target sequences with significant homology to other coding sequences. The homology search can be performed using BLAST, which can be found on the NCBI server on the world wide web.

3. Select qualifying target sequences for synthesis. At Ambion, preferably several target sequences can be selected along the length of the gene for evaluation.

The antisense oligonucleotide or siRNA of the invention inhibit the expression of the polypeptide of the invention and is thereby useful for suppressing the biological activity of the polypeptide of the invention. The length of the antisense oligonucleotides and siRNAs is at least 10 nucleotides and may be as long as the naturally occurring the transcript. Preferably, the antisense oligonucleotides and siRNAs have 19-25 nucleotides. Most preferably, the antisense oligonucleotides and siRNAs are less than 75, 50, 25 nucleotides in length.

Also, expression-inhibitors, comprising the antisense oligonucleotide or siRNA of the invention, are useful in the point that they can inhibit the biological activity of the polypeptide of the invention. Therefore, a composition comprising the antisense oligonucleotide or siRNA of the present invention is useful in treating a cell proliferative disease such as prostate cancer.

Furthermore, the present invention provides ribozymes that inhibit the expression of the MICAL2-PV or PCOTH polypeptide of the present invention.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi et al., FEBS LErr 228: 225 (1988)) and hairpin type ribozymes (Buzayan, Nature 323: 349 (1986); Kikuchi and Sasaki, Nucleic Acids Res 19: 6751 (1992)) are included in the small ribozymes. Methods for designing and constructing ribozymes are known in the art (see Koizumi et al., FEBS Lett 228: 225 (1988); Koizumi et al., Nucleic Acids Res 17: 7059 (1989);Kikuchi and Sasaki, Nucleic Acids Res 19: 6751(1992)). Thus, ribozymes inhibiting the expression of the polypeptides of the present invention can also be constructed based on their sequence information (SEQ ID NO: 1, 3 or 5) and these conventional methods.

Ribozymes against MICAL2-PV or PCOTH gene inhibit the expression of over-expressed MICAL2-PV or PCOTH protein and is thus useful for suppressing the biological activity of the protein. Therefore, the ribozymes are useful in treating or preventing prostate cancer.

Diagnosing Prostate Cancer

Moreover, the present invention provides a method for diagnosing cell proliferative disease such as prostate cancer using the expression level of the polypeptides of the present invention as a diagnostic marker.

This diagnosing method comprises the steps of: (a) detecting the expression level of the MICAL2-PV or PCOTH gene of the present invention; and (b) relating an elevation of the expression level to prostate cancer.

The expression levels of the MICAL2-PV or PCOTH gene in a biological sample can be estimated by quantifying mRNA corresponding to or protein encoded by the MICAL2-PV or PCOTH gene. Quantification methods for mRNA are known to those skilled in the art. For example, the levels of mRNAs corresponding to the MICAL2-PV or PCOTH gene can be estimated by Northern blotting or RT-PCR. Since the full-length nucleotide sequences of the MICAL2-PV or PCOTH genes are shown in SEQ ID NO: 1, 3 or 5, anyone skilled in the art can design the nucleotide sequences for probes or primers to quantify the MICAL2-PV or PCOTH gene.

Also the expression level of the MICAL2-PV or PCOTH gene can be analyzed based on the activity or quantity of protein encoded by the gene. A method for determining the quantity of the MICAL2-PV or PCOTH protein is shown in bellow. For example, immunoassay method is useful for the determination of the proteins in biological materials. Any biological materials can be used as the biological sample for the determination of the protein or it's activity so long as the marker gene (MICAL2-PV or PCOTH gene) is expressed in the sample of a prostate cancer patient. For example, prostate duct epithelium can be mentioned as such biological sample. However, bodily fluids such as blood and urine may be also analyzed. On the other hand, a suitable method can be selected for the determination of the activity of a protein encoded by the MICAL2-PV or PCOTH gene according to the activity of each protein to be analyzed.

Expression levels of the MICAL2-PV or PCOTH gene in a biological sample are estimated and compared with those in a normal sample (sample derived from a non-diseased subject). When such a comparison shows that the expression level of the target gene is higher than those in the normal sample, the subject is judged to be affected with prostate cancer. The expression level of MICAL2-PV or PCOTH gene in the biological samples from a normal subject and subject to be diagnosed may be determined at the same time. Alternatively, normal ranges of the expression levels can be determined by a statistical method based on the results obtained by analyzing the expression level of the gene in samples previously collected from a control group. A result obtained by comparing the sample of a subject is compared with the normal range; when the result does not fall within the normal range, the subject is judged to be affected with or is at risk of developing prostate cancer.

In the present invention, a diagnostic agent for diagnosing cell proliferative disease, such as prostate cancer, is also provided. The diagnostic agent of the present invention comprises a compound that binds to a polynucleotide or a polypeptide of the present invention. Preferably, an oligonucleotide that hybridizes to the polynucleotide of the present invention or an antibody that binds to the polypeptide of the present invention may be used as such a compound.

The present method of diagnosing prostate cancer may be applied for assessing the efficacy of treatment of prostate cancer in a subject. According to the method, a biological sample, such as a test cell population, is obtained from a subject undergoing treatment for prostate cancer. The method for assessment can be conducted according to conventional methods of diagnosing prostate cancer.

If desired, biological samples are obtained from the subject at various time points before, during or after the treatment. The expression level of MICAL2-PV or PCOTH gene, in the biological sample is then determined and compared to a control level derived, for example, from a reference cell population which includes cells whose state of prostate cancer (i.e., cancerous cell or non-cancerous cell) is known. The control level is determined in a biological sample that has not been exposed to the treatment.

If the control level is derived from a biological sample which contains no cancerous cell, a similarity between the expression level in the subject-derived biological sample and the control level indicates that the treatment is efficacious. A difference between the expression level of the MICAL2-PV or PCOTH gene in the subject-derived biological sample and the control level indicates a less favorable clinical outcome or prognosis.

The term "efficacious" refers that the treatment leads to a reduction in the expression of a pathologically up-regulated gene (MICAL2-PV or PCOTH gene) or a decrease in size, prevalence or proliferating potential of prostate cancer cells in a subject. When a treatment is applied prophylactically, "efficacious" indicates that the treatment retards or prevents occurrence of prostate cancer. The assessment of prostate cancer can be made using standard clinical protocols. Furthermore, the efficaciousness of a treatment is determined in association with any known method for diagnosing or treating prostate cancer.

Moreover, the present method of diagnosing prostate cancer may also be applied for assessing the prognosis of a subject with prostate cancer by comparing the expression level of MICAL2-PV or PCOTH gene in a patient-derived biological sample, such as test cell population, to a control level. Alternatively, the expression level of MICAL2-PV or PCOTH gene in a biological sample derived from patients may be measured over a spectrum of disease stages to assess the prognosis of the patient.

An increase in the expression level of MICAL2-PV or PCOTH gene compared to a normal control level indicates less favorable prognosis. A decrease in the expression level of MICAL2-PV or PCOTH gene indicates a more favorable prognosis for the patient.

Screening Compounds

Using the MICAL2-PV or PCOTH gene, proteins encoded by the gene or transcriptional regulatory region of the gene, compounds can be screened that alter the expression of the gene or the biological activity of a polypeptide encoded by the gene. Such compounds are expected to serve as pharmaceuticals for treating or preventing prostate cancer.

Therefore, the present invention provides a method of screening for a compound for treating or preventing prostate cancer using the polypeptide of the present invention. An embodiment of this screening method comprises the steps of: (a) contacting a test compound with a polypeptide of the present invention; (b) detecting the binding activity between the polypeptide of the present invention and the test compound; and (c) selecting the compound that binds to the polypeptide of the present invention.

The polypeptide of the present invention to be used for screening may be a recombinant polypeptide or a protein derived from the nature or a partial peptide thereof. The polypeptide of the present invention to be contacted with a test compound can be, for example, a purified polypeptide, a soluble protein, a form bound to a carrier or a fusion protein fused with other polypeptides.

As a method of screening for proteins, for example, that bind to the polypeptide of the present invention using the polypeptide of the present invention, many methods well known by a person skilled in the art can be used. Such a screening can be conducted by, for example, immunoprecipitation method, specifically, in the following manner. The gene encoding the polypeptide of the present invention is expressed in animal cells and so on by inserting the gene to an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1982)), the EF-α promoter (Kim et al., Gene 91: 217-23 (1990)), the CAG promoter (Niwa et al., Gene 108: 193-200 (1991)), the RSV LTR promoter (Cullen, Methods in Enzymology 152: 684-704 (1987)) the SRα promoter (Takebe et al., Mol Cell Biol 8: 466 (1988)), the CMV immediate early promoter (Seed and Aruffo, Proc Natl Acad Sci USA 84: 3365-9 (1987)), the SV40 late promoter (Gheysen and Fiers, J Mol Appl Genet 1: 385-94 (1982)), the Adenovirus late promoter (Kaufman et al., Mol Cell Biol 9: 946 (1989)), the HSV TK promoter and so on. The introduction of the gene into animal cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1642-3 (1985)), the Lipofectin method (Derijard, B Cell 7: 1025-37 (1994); Lamb et al., Nature Genetics 5: 22-30 (1993): Rabindran et al., Science 259: 230-4 (1993)) and so on. The polypeptide of the present invention can be expressed as a fusion protein comprising a recognition site (epitope) of a monoclonal antibody by introducing the epitope of the monoclonal antibody, whose specificity has been revealed, to the N- or C-terminus of the polypeptide of the present invention. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the polypeptide of the present invention by the fusion is also reported. Epitopes, such as polyhistidine (His-tag), influenza aggregate HA, human c-myc, FLAG Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the polypeptide of the present invention (Experimental Medicine 13: 85-90 (1995)).

In immunoprecipitation, an immune complex is formed by adding these antibodies to cell lysate prepared using an appropriate detergent. The immune complex consists of the polypeptide of the present invention, a polypeptide comprising the binding ability with the polypeptide, and an antibody. Immunoprecipitation can be also conducted using antibodies against the polypeptide of the present invention, besides using antibodies against the above epitopes, which antibodies can be prepared as described above.

An immune complex can be precipitated, for example by Protein A sepharose or Protein G sepharose when the antibody is a mouse IgG antibody. If the polypeptide of the present invention is prepared as a fusion protein with an epitope, such as GST, an immune complex can be formed in the same manner as in the use of the antibody against the polypeptide of the present invention, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the polypeptide of the present invention is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening proteins binding to the polypeptide of the present invention using the polypeptide, for example, West-Western blotting analysis (Skolnik et al., Cell 65: 83-90 (1991)) can be used. Specifically, a protein binding to the polypeptide of the present invention can be obtained by preparing a cDNA library from cells, tissues, organs (for example, tissues such as testis for MICAL2-PV, and testis or prostate for PCOTH), or cultured cells (e.g., LNCaP, PC3, DU145) expected to express a protein binding to the polypeptide of the present invention using a phage vector (e.g., ZAP), expressing the protein on LB-agarose, fixing the protein expressed on a filter, reacting the purified and labeled polypeptide of the present invention with the above filter, and detecting the plaques expressing proteins bound to the polypeptide of the present invention according to the label. The polypeptide of the invention may be labeled by utilizing the binding between biotin and avidin, or by utilizing an antibody that specifically binds to the polypeptide of the present invention, or a peptide or polypeptide (for example, GST) that is fused to the polypeptide of the present invention. Methods using radioisotope or fluorescence arid such may be also used.

Alternatively, in another embodiment of the screening method of the present invention, a two-hybrid system utilizing ceils may be used ("MATCHMAKER Two-Hybrid system", "Mammalian MATCHMAKER Two-Hybrid Assay Kit", i "MATCHMAKER one-Hybrid system" (Clontech); "HybriZAP™ Two-Hybrid Vector System" (Stratagene); the references "Dalton and Treisman, Cell 68:597-612 (1992)", "Fields and Stemglanz, Trends Genet 10:286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to E. coli and expressing the protein.

As a reporter gene, for example, Ade2 gene, lacZ gene, CAT gene, luciferase gene and such can be used in addition to the HIS3 gene.

A compound binding to the polypeptide of the present invention can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore™, Pharmacia). Therefore, it is possible to evaluate the binding between the polypeptide of the invention and a test compound using a biosensor such as BIAcore™.

The methods of screening for molecules that bind when the immobilized polypeptide of the present invention is exposed to synthetic chemical compounds, or natural substance banks or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the protein of the present invention (including agonist and antagonist) are well known to one skilled in the art.

Alternatively, the present invention provides a method of screening for a compound for treating or preventing prostate cancer using the polypeptide of the present invention comprising the steps as follows:

(a) contacting a test compound with the polypeptide of the present invention;

(b) detecting the biological activity of the polypeptide of step (a); and (c) selecting a compound that suppresses the biological activity of the polypeptide in comparison with the biological activity detected in the absence of the test compound.

Since the MICAL2-PV and PCOTH proteins of the present invention have the activity of promoting cell proliferation of prostate cancer cells, a compound which promotes or inhibits this activity of one of these proteins of the present invention can be screened using this activity as an index.

Any polypeptides can be used for screening so long as they comprise the biological activity of the MICAL2-PV or PCOTH protein. Such biological activity include cell-proliferating activity of the human MICAL2-PV or PCOTH protein, the activity of MICAL2-PV to bind to actin. For example, a human MICAL2-PV or PCOTH protein can be used and polypeptides functionally equivalent to these proteins can also be used. Such polypeptides may be expressed endogenously or exogenously by cells.

The compound isolated by this screening is a candidate for agonists or antagonists of the polypeptide of the present invention. The term "agonist" refers to molecules that activate the function of the polypeptide of the present invention by binding thereto. Likewise, the term "antagonist" refers to molecules that inhibit the function of the polypeptide of the present invention by binding thereto. Moreover, a compound isolated by this screening is a candidate for compounds which inhibit the in vivo interaction of the polypeptide of the present invention with molecules (including DNAs and proteins).

When the biological activity to be detected in the present method is cell proliferation, it can be detected, for example, by preparing cells which express the polypeptide of the present invention, culturing the cells in the presence of a test compound, and determining the speed of cell proliferation, measuring the cell cycle and such, as well as by measuring the colony forming activity as described in the Examples.

In a further embodiment, the present invention provides methods for screening compounds for treating or preventing prostate cancer. As discussed in detail above, by controlling the expression levels of the MICAL2-PV or PCOTH, one can control the onset and progression of prostate cancer. Thus, compounds that may be used in the treatment or prevention of prostate cancer can be identified through screenings that use the expression levels of MICAL2-PV or PCOTH as indices. In the context of the present invention, such screening may comprise, for example, the following steps:

a) contacting a test compound with a cell expressing the MICAL2-PV or PCOTH, and b) selecting a compound that reduces the expression level of MICAL2-PV or PCOTH in comparison with the expression level detected in the absence of the test compound.

Cells expressing at least one of the MICAL2-PV or PCOTH include, for example, cell lines established from prostate cancers; such cells can be used for the above screening of the present invention (e.g., LNCaP, PC3, DU145). The expression level can be estimated by methods well known to one skilled in the art. In the method of screening, a compound that reduces the expression level of at least one of MICAL2-PV or PCOTH can be selected as candidate agents to be used for the treatment or prevention of prostate cancer.

Alternatively, the screening method of the present invention may comprise the following steps:

a) contacting a test compound with a cell into which a vector comprising the transcriptional regulatory region of one or more marker genes and a reporter gene that is expressed under the control of the transcriptional regulatory region has been introduced, wherein the one or more marker genes are MICAL2-PV and PCOTH, b) measuring the activity of said reporter gene; and c) selecting a compound that reduces the expression level of said reporter gene as compared to a control.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

In a further embodiment of the method for screening a compound for treating or preventing prostate cancer of the present invention, the method utilizes the binding ability of MICAL2-PV to actin. The MICAL2-PV protein of the present invention was revealed to comprise a domain having homology to calponin domain, an actin-binding domain. Therefore, the protein encoded by MICAL2-PV is predicted to interact with actin or other microtubles. These domains cross-link actin filaments into bundles and networks. The finding suggest that the MICAL2-PV protein of the present invention exerts the function of cell proliferation via its binding to molecules, such as acting and other microtubles. Thus, it is expected that the inhibition of the binding between the MICAL2-PV protein and actin or other microtubles leads to the suppression of cell proliferation, and compounds inhibiting the binding serve as pharmaceuticals for treating or preventing prostate cancer.

This screening method includes the steps of: (a) contacting a MICAL-PV polypeptide of the present invention with actin in the presence of a test compound; (b) detecting the binding between the polypeptide and actin; and (c) selecting the compound that inhibits the binding between the polypeptide and actin.

The MICAL2-PV polypeptide of the present invention and actin to be used for the screening may be a recombinant polypeptide or a protein derived from the nature, or may also be a partial peptide thereof so long as it retains the binding ability to each other. The MICAL2-PV polypeptide and actin to be used in the screening can be, for example, a purified polypeptide, a soluble protein, a form bound to a carrier or a fusion protein fused with other polypeptides.

As a method of screening for compounds that inhibit the binding between the MICAL2-PV protein and actin, many methods well known by one skilled in the art can be used. Such a screening can be carried out as an in vitro assay system, for example, in a cellular system. More specifically, first, either the MICAL2-PV polypeptide or actin is bound to a support, and the other protein is added together with a test compound thereto. Next, the mixture is incubated, washed and the other protein bound to the support is detected and/or measured.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they bay be filled into a column.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore™, Pharmacia). Therefore, it is possible to evaluate the binding between the MICAL2-PV polypeptide and actin using a biosensor such as BIAcore™.

Alternatively, either the MICAL2-PV polypeptide or actin may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances such as radioisotope (erg., $^3$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiosyanete (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, the binding of the MICAL2-PV polypeptide and actin can be also detected or measured using antibodies to the MICAL2-PV polypeptide and actin. For example, after contacting the MICAL2-PV polypeptide immobilized on a support with a test compound and actin, the mixture is incubated and washed, and detection or measurement can be conducted using an antibody against actin. Alternatively, actin may be immobilized on a support, and an antibody against MICAL2-PV may be used as the antibody.

In case of using an antibody in the present screening, the antibody is preferably labeled with one of the labeling substances mentioned above, and detected or measured based on the labeling substance. Alternatively, the antibody against the MICAL2-PV polypeptide or actin may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", i "MATCHMAKER one-Hybrid system" (Clontech); "HybriZAP™ Two-Hybrid Vector System" (Stratagene); the references "Dalton and Treisman, Cell 68:597-612 (1992)", "Fields and Stemglanz, Trends Genet 10:286-92 (1994)").

In the two-hybrid system, the MICAL2-PV polypeptide of the invention is fused to the SRF-binding region or GAL4-binding region and expressed in yeast cells. The actin binding to the MICAL2-PV polypeptide of the invention is fused to the VP16 or GAL4 transcriptional activation region and also expressed in the yeast cells in the existence of a test compound. When the test compound does not inhibit the binding between the MICAL2-PV polypeptide and actin, the binding of the two activates a reporter gene, making positive clones detectable.

As a reporter gene, for example, Ade2 gene, lacZ gene, CAT gene, luciferase gene and such can be used besides HIS3 gene.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam (1997) Anticancer Drug Des. 12: 145). Examples of methods for the synthesis of molecular libraries can be found in the art (DeWitt et al. (1993) Proc. Natl. Acad. Sci. USA 90: 6909; Erb et al. (1994) Proc. Natl. Acad. Sci. USA 91: 11422; Zuckermann et al. (1994) J. Med. Chem. 37: 2678; Cho et al. (1993) Science 261: 1303; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233). Libraries of compounds may be presented in solution (see Houghten (1992) Bio/Techniques 13: 412) or on beads (Lam (1991) Nature 354: 82), chips (Fodor (1993) Nature 364: 555), bacteria (U.S. Pat. No. 5,223,409), spores (U.S. Pat. Nos. 5,571,698; 5,403,484, and 5,223,409), plasmids (Cull et al. (1992) Proc. Natl. Acad. Sci. USA 89: 1865) or phage (Scott and Smith (1990) Science 249: 386; Delvin (1990) Science 249: 404; Cwirla et al. (1990) Proc. Natl. Acad. Sci. USA 87: 6378; Felici (1991) J. Mol. Biol. 222: 301; US Pat. Application 2002103360).

A compound isolated by the screening methods of the present invention is a candidate for drugs which promote or inhibit the activity of the polypeptide of the present invention, for treating or preventing diseases attributed to, for example, cell proliferative diseases, such as prostate cancer. A compound in which a part of the structure of the compound obtained by the present screening methods of the present invention is converted by addition, deletion and/or replacement, is included in the compounds obtained by the screening methods of the present invention.

Pharmaceutical Compositions for Treating or Preventing Prostate Cancer

The present invention provides compositions for treating or preventing prostate cancer comprising any of the compounds selected by the screening methods of the present invention.

When administrating a compound isolated by the screening methods of the present invention as a pharmaceutical for humans or other mammals, such as mice, rats, guinea-pigs, rabbits, cats, dogs, sheep, pigs, cattle, monkeys, baboons, chimpanzees, for treating a cell proliferative disease (e.g., prostate cancer) the isolated compound can be directly administered or can be formulated into a dosage form using known pharmaceutical preparation methods. For example, according to the need, the drugs can be taken orally, as sugarcoated tablets, capsules, elixirs and microcapsules; or non-orally, in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agents, surfactants, stabilizers, flavoring agents, excipients, vehicles, preservatives, binders and such, in a unit dose form required for generally accepted drug implementation. The amount of active ingredients in these preparations makes a suitable dosage within the indicated range acquirable.

Examples of additives that can be mixed to tablets and capsules are, binders such as gelatin, corn starch, tragacanth gum and arabic gum; excipients such as crystalline cellulose; swelling agents such as corn starch, gelatin and alginic acid; lubricants such as magnesium stearate; sweeteners such as sucrose, lactose or saccharin; flavoring agents such as peppermint, Gaultheria adenothrix oil and cherry. When the unit dosage form is a capsule, a liquid carrier, such as oil, can also be further included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizers and may be formulated with a buffer, such as phosphate buffer and sodium acetate buffer; a pain-killer, such as procaine hydrochloride; a stabilizer, such as benzyl alcohol, phenol; and an anti-oxidant. The prepared injection may be filled into a suitable ampule.

Methods well known to one skilled in the art may be used to administer the inventive pharmaceutical compound to patients, for example as intraarterial, intravenous, percutaneous injections and also as intranasal, transbronchial, intramuscular or oral administrations. The dosage and method of administration vary according to the body-weight and age of a patient and the administration method; however, one skilled in the art can routinely select them. If said compound is encodable by a DNA, the DNA can, be inserted into a vector for gene therapy and the vector administered to perform the therapy. The dosage and method of administration vary according to the body-weight, age, and symptoms of a patient but one skilled in the art can select them suitably.

For example, although there are some differences according to the symptoms, the dose of a compound that binds with the polypeptide of the present invention and regulates its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

Furthermore, the present invention provides pharmaceutical compositions for treating or preventing prostate cancer comprising active ingredients that inhibits the expression of MICAL2-PV or PCOTH gene. Such active ingredients include antisense polynucleotides, siRNAs or ribozymes against the MICAL2-PV or PCOTH gene or derivatives, such as expression vector, of the antisense polynucleotides, siRNAs or ribozymes.

These active ingredients can be made into an external preparation, such as a liniment or a poultice, by mixing with a suitable base material which is inactive against the derivatives. Also, as needed, they can be formulated into tablets, powders, granules, capsules, liposome capsules, injections, solutions, nose-drops and freeze-drying agents by adding excipients, isotonic agents, solubilizers, stabilizers, preservatives, pain-killers and such. These can be prepared according to conventional methods.

The active ingredient is given to the patient by directly applying onto the ailing site or by injecting into a blood vessel so that it will reach the site of ailment. A mounting medium can also be used to increase durability and membrane-permeability. Examples of mouting medium includes liposome, poly-L-lysine, lipid, cholesterol, lipofectin or derivatives of these.

The dosage of such compositions of the present invention can be adjusted suitably according to the patient's condition and used in desired amounts. For example, a dose range of 0.1 to 100 mg/kg, preferably 0.1 to 50 mg/kg can be administered.

Another embodiment of the present invention is a composition for treating or preventing prostate cancer comprising an antibody against a polypeptide encoded by the MICAL2-PV or PCOTH gene or fragments of the antibody that bind to the polypeptide.

Although there are some differences according to the symptoms, the dose of an antibody or fragments thereof for treating or preventing prostate cancer is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the condition of the patient, symptoms of the disease and method of a se dministration, it is convenient to intravenously inject a dose of about 0.01 mg to about 30 mg per day, preferably about 0.1 to about 20 mg per day and more preferably about 0.1 to about 10 mg per day. A the caof other animals too, it is possible to administer an amount converted to 60 kg of body-weight.

Methods for Treating or Preventing Prostate Cancer

The invention provides a method for treating or preventing prostate cancer in a subject. Therapeutic compounds are administered prophylactically or therapeutically to subject suffering from or at risk of (or susceptible to) developing prostate cancer. Such subjects are identified using standard clinical methods or by detecting an aberrant expression level or activity of MICAL2-PV or PCOTH. Prophylactic administration occurs prior to the manifestation of overt clinical symptoms of disease, such that a disease or disorder is prevented or, alternatively, delayed in its progression.

The therapeutic method includes decreasing the expression or function, or both of MICAL2-PV or PCOTH gene. In these methods, the subject is treated with an effective amount of a compound, which decreases one or both of the over-expressed genes (MICAL2-PV or PCOTH gene) in the subject. Administration can be systemic or local. Therapeutic compounds include compounds that decrease the expression level of such gene endogenously existing in the prostate cancerous cells (i.e., compounds that down-regulate the expression of the over-expressed gene(s)). Administration of such therapeutic compounds counter the effects of aberrantly-over expressed gene(s) in the subjects cells and are expected to improve the clinical condition of the subject. Such compounds can be obtained by the screening method of the present invention described above.

The expression of MICAL2-PV or PCOTH gene may be also inhibited in any of several ways known in the art including administering to the subject a nucleic acid that inhibits or antagonizes the expression of the gene(s). Antisense oligonucleotides, siRNA or ribozymes which disrupts expression of the gene(s) can be used for inhibiting the expression of the genes.

As noted above, antisense-oligonucleotides corresponding to the nucleotide sequence of MICAL2-PV or PCOTH gene can be used to reduce the expression level of the MICAL2-PV or PCOTH gene. Specifically, the antisense-oligonucleotides of the present invention may act by binding to any of the polypeptides encoded by the MICAL2-PV or PCOTH gene, or mRNAs corresponding thereto, thereby inhibiting the transcription or translation of the genes, promoting the degradation of the mRNAs, and/or inhibiting the expression of proteins encoded by the genes, and finally inhibiting the function of the MICAL2-PV or PCOTH proteins.

An antisense-oligonucleotides and derivatives thereof can be made into an external preparation, such as a liniment or a poultice, by mixing with a suitable base material which is inactive against the derivative and used in the method for treating or preventing prostate cancer of the present invention.

The nucleic acids that inhibit one or more gene products of over-expressed genes also include small interfering RNAs (siRNA) comprising a combination of a sense strand nucleic acid and an antisense strand nucleic acid of the nucleotide sequence encoding the MICAL2-PV or PCOTH gene. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, e.g., a hairpin.

The method is used to suppress gene expression of a cell with up-regulated expression of the MICAL2-PV or PCOTH gene. Binding of the siRNA to the MICAL2-PV or PCOTH gene transcript in the target cell results in a reduction of MICAL2-PV or PCOTH protein production by the cell.

The nucleic acids that inhibit one or more gene products of over-expressed genes also include ribozymes against the over-expressed gene(s) (MICAL2-PV or PCOTH gene).

Moreover, the present invention provides a method for treating or preventing a cell proliferative disease, such as prostate cancer, using an antibody against the polypeptide of the present invention. According to the method, a pharmaceutically effective amount of an antibody against the polypeptide of the present invention is administered. Since the expression of the MICAL2-PV and PCOTH protein are up-regulated in prostate cancer cells and the suppression of the expression of these proteins leads to the decrease in cell proliferating activity, it is expected that cell proliferative diseases can be treated or prevented by binding the antibody and these proteins. Thus, an antibody against the polypeptide of the present invention are administered at a dosage sufficient to reduce the activity of the protein of the present invention, which is in the range of 0.1 to about 250 mg/kg per day. The dose range for adult humans is generally from about 5 mg to about 17.5 g/day, preferably about 5 mg to about 10 g/day, and most preferably about 100 mg to about 3 g/day.

Alternatively, an antibody binding to a cell surface marker specific for tumor cells can be used as a tool for drug delivery. For example, the antibody conjugated with a cytotoxic agent is administered at a dosage sufficient to injure tumor cells.

The present invention also relates to a method of inducing anti-tumor immunity comprising the step of administering MICAL2-PV or PCOTH protein or an immunologically active fragment thereof, or a polynucleotide encoding the protein or fragments thereof. The MICAL2-PV or PCOTH protein or the immunologically active fragments thereof are useful as vaccines against cell proliferative diseases such as prostate cancer. In some cases the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, vaccine against cell proliferative disease refers to a substance that has the function to induce anti-tumor immunity upon inoculation into animals. In general, anti-tumor immunity includes immune responses such as follows:lso, in induction of cytotoxic lymphocytes against tumors, induction of antibodies that recognize tumors, and induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils, and NK cells. Since CD4+ T cells and CD8+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC, and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DC, peripheral blood mononuclear cells (PBMCs) may also be used as the APC. The induction of CTL is reported that the it can be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against tumors. Furthermore, APC that acquired the ability to induce CTL against tumors by contacting with the polypeptides are useful as vaccines against tumors. Furthermore, CTL that acquired cytotoxicity due to presentation of the polypeptide antigens by APC can be also used as vaccines against tumors. Such therapeutic methods for tumors using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide and when growth of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of cell proliferating diseases, such as prostate cancers. Therapy against cancer or prevention of the onset of cancer includes any of the steps, such as inhibition of the growth of cancerous cells, involution of cancer and suppression of occurrence of cancer. Decrease in mortality of individuals having cancer, decrease of tumor markers in the blood, alleviation of detectable symptoms accompanying cancer and such are also included as the effect of therapy or prevention of cancer. Such therapeutic and preventive effects are preferably statistically significant For example, in observation, at a significance level of 5% or less, wherein the therapeutic or preventive effect of a vaccine against cell proliferative diseases is compared to a control without vaccine administration. For example, Student's t-test, the Mann-Whitney U-test or ANOVA may be used for statistical analyses.

The above-mentioned protein having immunological activity or a vector encoding the protein may be combined with an adjuvant. An adjuvant refers to a compound that enhances the immune response against the protein when administered together (or successively) with the protein having immunological activity. Examples of adjuvants include cholera toxin, salmonella toxin, alum and such, but are not limited thereto. Furthermore, the vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, tumors can be treated or prevented, for example, by the ex vivo method. More specifically, PBMCs of a subject receiving treatment or prevention therapy are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of tumors from other individuals.

Furthermore, a pharmaceutical composition for treating or preventing a cell proliferative disease, such as prostate cancer, comprising a pharmaceutically effective amount of the MICAL2-PV or PCOTH polypeptide is provided. The pharmaceutical composition may be used for raising anti tumor immunity. The normal expression of MICAL2-PV is restricted to testis and that of PCOTH is restricted to testis and prostate. Therefore, suppression of these genes may not adversely affect other organs. Thus, the MICAL2-PV and PCOTH polypeptides are preferable for treating cell proliferative disease, especially prostate cancers. Furthermore, since peptide fragments of proteins specifically expressed in cancerous cells were revealed to induce immune response against the cancer, peptide fragments of MICAL2-PV or PCOTH can also be used in a pharmaceutical composition for treating or preventing cell proliferative diseases such as prostate cancers. In the present invention, the polypeptide or fragment thereof is administered at a dosage sufficient to induce anti-tumor immunity, which is in the range of 0.1 mg to 10 mg, preferably 0.3 mg to 5 mg, more preferably 0.8 mg to 1.5 mg. The administrations are repeated. For example, 1 mg of the peptide or fragment thereof may be administered 4 times in every two weeks for inducing the anti-tumor immunity.

In addition, polynucleotides encoding MICAL2-PV or PCOTH, or fragments thereof may be used for raising anti tumor immunity. Such polynucleotides may be incorporated in an expression vector to express MICAL2-PV or PCOTH, or fragments thereof in a subject to be treated. Thus, the present invention encompasses method for inducing anti tumor immunity wherein the polynucleotides encoding MICAL2-PV or PCOTH, or fragments thereof are administered to a subject suffering or being at risk of developing cell proliferative diseases such as prostate cancer.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications cited herein are incorporated by reference.

BEST MODE FOR CARRYING OUT THE INVENTION

The present invention is illustrated in details by following Examples, but is not restricted to these Examples.

1. Materials and Methods (1) Cell Lines and Clinical Materials

Human prostate cancer cells LNCaP, PC3 and DU145 were purchased from the American Type Culture Collection (ATCC, Rockville, Md.). All cells were cultured in RPMI-1640 (Sigma, St. Louis, Mo.) for LNCap, Dulbecco's modified Eagle's medium (Invitrogen, Carlsbad, Calif.) for DU145, and F12 nutrient mixture (Invitrogen, Carlsbad, Calif.) for PC3, each supplemented with 10% fetal bovine serum and 1% antibiotic/antimycotic solution (Sigma).

(2) Isolation of Two Novel Human Genes Using cDNA Microarray

Fabrication of cDNA microarray slides has been described (Ono et al., Cancer Res 60: 5007-11 (2000)). For each analysis of expression profiles, the present inventors prepared duplicate sets of cDNA microarray slides containing 23,040 cDNA spots, to reduce experimental fluctuation. Briefly, total RNAs were purified from prostate cancer cells and normal prostate duct epithelium microdissected from 20 prostate cancer tissues. T7-based RNA amplification was carried out to obtain adequate RNA for microarray experiments. Aliquots of amplified RNA from prostate cancer cells and normal duct epithelium were labeled by reverse transcription with Cy5-dCTP and Cy3-dCTP, respectively (Amersham Biosciences, Buckinghamshire, UK). Hybridization, washing, and detection were carried out as described previously (Ono et al., Cancer Res 60: 5007-11 (2000)). Subsequently, among the up-regulated genes, two genes with in-house identification number D4493 and A5736 were focused due to its expression ratio which was greater than 5.0 in more than 50% of informative prostate cancers and their expression level in normal vital major organs which was relatively low according to previous data obtained by the inventors on gene expression in 29 normal human tissues (Saito-Hisaminato et al., DNA Res 9: 35-45 (2002)).

(3) Northern-blot Analysis

Human multiple-tissue Northern blots (Clontech, Palo Alto, Calif.) were hybridized with an [$\alpha$-$^{32}$P] dCTP-labeled PCR product of D4493 and A5736. The PCR products were prepared by RT-PCR using primers: 5'-CCGA-CACTCTGGGTAGGAGA-3'(SEQ.ID.NO.7) and 5'-TACGTGAGCTCTGAGGACCA-3'(SEQ.ID.NO.8) for D4493; and 5'-TGAAGCAACAAAGAGAGGAGGAG-3' (SEQ.ID.NO.9) and 5'-CCGTGTGGCACTGTAAAT-GATTA-3'(SEQ.ID.NO.10) for A5736. Pre-hybridization, hybridization and washing were performed according to the supplier's recommendations. The blots were autoradiographed with intensifying screens at −80° C. for 7 days.

(4) Semi-quantitative RT-PCR Analysis

Total RNA was extracted from cultured cells and clinical samples using TRIzol™ Reagent (Invitrogen) according to the manufacturer's protocol. Extracted RNA was treated with DNase I (Roche) and reversely transcribed for single-stranded eDNAs using oligo(dT)I6 primer with Superscript™ II reverse transcriptase (Roche). Appropriate dilutions of each single-stranded eDNA were prepared for subsequent PCR amplification by monitoring the 13-actin (ACTB) as a quantitative control. The primer sequences were 5'-CATCCACGAAACTACCTTCAACT-3' (SEQ.ID.NO. 11) and 5'-TCTCCTTAGAGAGAAGTGGGGTG-3' (SEQ.ID.NO. 12) for ACTB;

5'-CCGACACTCTGGGTAGGAGA-3' (SEQ.ID.NO. 13) and 5'-TACGTGAGCTCTGAGGACCA-3' (SEQ.ID.NO.14) for D4493; and 5'-GCAGGGATATCTTTGAGAAA-3' (SEQ.ID.NO. 15) and 5'-CCAGGATCTGCACAAATACA-3' (SEQ.ID.NO. 16) for A5736. All reactions involved initial denaturation at 94° C. for 2 min followed by 21 cycles (for ACTB) or 35 cycles (for D4493 and A5736) at 94° C. for 30 s, 58° C. for 30 s, and 72° C. for 1 min, on a GeneAmp™ PCR system 9700 (PE Applied Biosystems).

(5) Construction of Expression Vector

The entire coding sequence of D4493 cDNA was amplified by RT-PCR with primers; 5'-CGTGGATCCC AGACCGTG-CATCATGGGCAC ATCTGAAGAA GGAAACTTGC-3' (SEQ.ID.NO.17) (D4493-forward) and 5'-AATCTCGAGT CAGGGGCAGAAGGGGAATAA GG-3'(SEQ.ID.NO.18) (D4493-reverse). The product was inserted into the EcoRI sites of pCAGGS neo vector after blunting treatment. For detection of D4493 protein expression, HA tag was fused at $NH_2$ or COOH terminus of the D4493 protein. The entire coding sequence of A5736 cDNA was also amplified by RT-PCR with primers; 5'-CCCAAGCTTA TGGGGGAAAA CGAGGATGA-3'(SEQ.ID.NO.19) (A5736-forward) and 5'-TTTTCCTTTT GCGGCCGCGC GGAGCTTGAC TGG-GAAGC-3'(SEQ.ID.NO.20) (D5736-reverse). The product was inserted into the Hind III and Not I sites of pcDNA3.1 (+)/myc-His (Invitrogen). These constructs were confirmed by DNA sequencing.

(6) Immunocytochemical Staining

COS7 cells were transfected transiently with pCAGGS neo-D4493 and pcDNA3.1 (-)-A5736-myc-His using FuGENE™ 6 (Roche) according to manufacture's instruction, then were fixed with 4% paraformaldehyde and permeablilized with 0.2% Triton X-100 in PBS for 3 min at room temperature. Next, the cells were covered with blocking solution (3% BSA/PBS containing 0.2% Triton X-100) for 30 min at room temperature, and incubated with a rat anti-HA antibody (Roche) or a rat anti-myc antibody (Sigma) in blocking solution for 60 min at room temperature. After washing with PBS, cells were stained by a FITC-conjugated anti-rat secondary antibody (Organon teknika), and Rhodamine-conjugated anti-mouse secondary antibody (ICN Biomedicals) for 60 min at room temperature. Specimen was mounted with VECTASHIELD (VECTOR Laboratories, Inc, Burlingame, Calif.) containing 4',6'-diamidine-2'-phenylindolendihydrochrolide (DAPI) and visualized with Spectral Confocal Scanning Systems (Leica).

(7) siRNA Expression Vector and Transfection to Prostate Cancer Cell siRNA expression vector (psiU6BX) were used for evaluating the effect or RNAi to the target genes. The U6 promoter was cloned into the upstream of the gene specific sequence (19nt sequence from the target transcript separated by a short spacer TTCAAGAGA from the reverse complement of the same sequence) and five thymidines as termination signal, furthermore neo cassette was integrated to provide resistance against Geneticin (Sigma). The target sequences for D4493 were 5'-TAGGGCCCATGGGGCCCGG-3'(SEQ.ID.NO.21) (si1), 5'-ACCAGTTGGGCCCAAAGGC-3'(SEQ.ID.NO.22) (si2), 5'-AGGCCCAATGTTGCCCCTT-3' (SEQ.ID.NO.23) (si3), 5'-TGTTGCCCCTTGGCCCCTC-3' (SEQ.ID.NO.24) (si4), and 5'-GAAGCAGCACGACTTCTTC-3'(SEQ.ID.NO.25) (EGFP), respectively. The target sequences for A5736 are 5'-GCTGCTGGCCTCCATATCA-3'(SEQ.ID.NO.26) (si1), 5'-TGCTTACAACTACTGCTAC-3'(SEQ.ID.NO.27) (si2), and 5'-CTACTGCTACATGTACGAG-3'(SEQ.ID.NO.28) (si3). The human prostate cancer cell lines LNCaP, PC3 and DU145 were plated onto 10-cm dishes ($5\times10^5$ cells/dish), and transfected with psiU6BX containing EGFP target sequence (psiU6BX-EGFP) and psiH1BX containing target sequence (psiU6BX-si1~4 of D4493 or si1~3 of A5736) using Lipofectamine 2000 (Invitrogen) according to manufacture's instruction. Cells were selected by treating with 500 mg/ml Geneticin for one week and preliminary cells were harvested for expression analysis of the target genes and analyzed by RT-PCR. The primers of RT-PCR were the same as described above. These cells were also stained by Giemsa solution and performed MTT assay.

2. Results (1) Identification of PCOTH and Prostate Cancer Variants of MICAL2 (MICAL2-PV) as Up-regulated Genes in Prostate Cancer Cells Gene-expression profiles of purified cancer cells from 20 prostate cancers were analyzed using cDNA microarray representing 23,040 human genes. As a result, 88 genes that were commonly up-regulated in prostate cancer cells were identified. Among the identified genes, one gene with an in-house code D4493 that was markedly up-regulated in more than 50% of prostate cancer was focused and validated for its over-expressed pattern in prostate cancer cells by RT-PCR (FIG. 1A). D4493 was overlapped by two ESTs (BC015452 and BG178505) derived from prostate cancer cDNA library and was revealed to be identical with LOC221179 (XP_167955). Comparison between mouse/rat genome sequences, a novel coding region of LOC221179 was determined which codes a 100-amino acid protein. Northern blot analysis demonstrated that LOC221179 was highly and locally expressed in prostate and testis (FIG. 1B). This product has one characteristic domain, collagen triple helix repeat (FIG. 1C), which is a characteristic feature of the collagen superfamily. Thus, the gene was dubbed "PCOTH (prostate collagen triple helix)".

Figure 2:
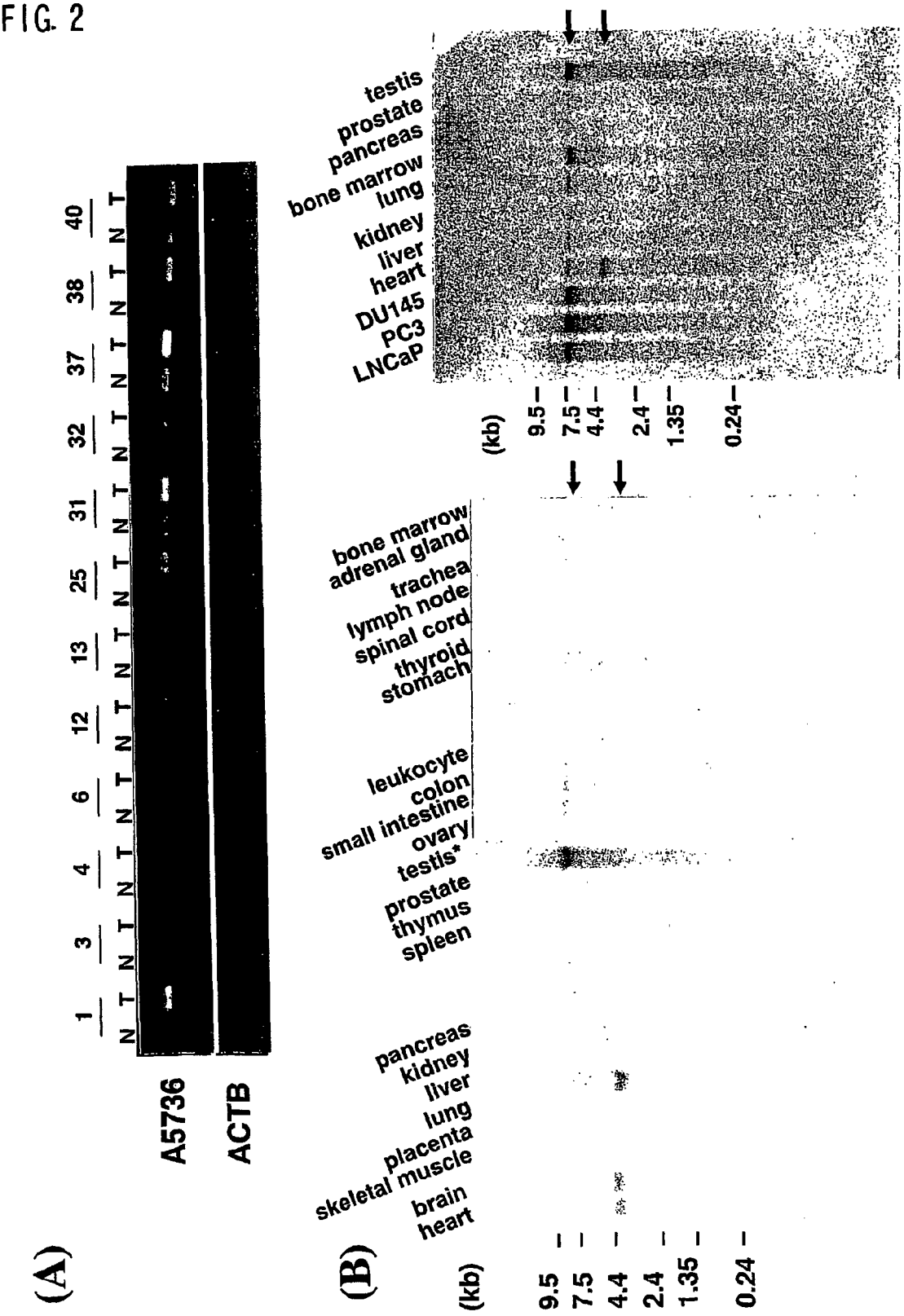
FIG. 2(A) depicts photographs showing the result of validation of over-expression of A5736 (MICAL2-PV) in prostate cancer cells by RT-PCR. The microdissected normal prostate duct epithelial cells (N) and prostate cancer cells (T) from the same individual were compared by semiquantitative RT-PCR. ACTB was used for normalization of the results. (B) depicts photographs showing the result of Northern blot analysis of normal human multiple tissues and prostate cancer cell lines. The approximately 7 kb transcript corresponding to MICAL2-PV was highly expressed in testis and prostate cancer cell lines (LNCaP, PC3 and DU145), while the approximately 4 kb transcript corresponding to the original MICAL2 was expressed in heart, brain and liver, but not in prostate cancer cell lines. (C) depicts an illustration showing the alignment of the exons of MICAL2 (KIAA0750) and MICAL2-PV. MICAL2 (KIAA0750) is a 3.8 kb transcript and consists of 28 exons, while MICAL2-PV is a 6.8 kb transcript in which several exons are deleted and consist of the long last exons. MICAL2-PV has two isoforms, long form (Accession number: AB110785) and short form (Accession number: AB110786) wherein one exon is deleted from the long form. The long form is predicted to yield a 976-amino acid protein that is different from the MICAL2 (KIAA0750) protein in its COOH region.
Figure 2:
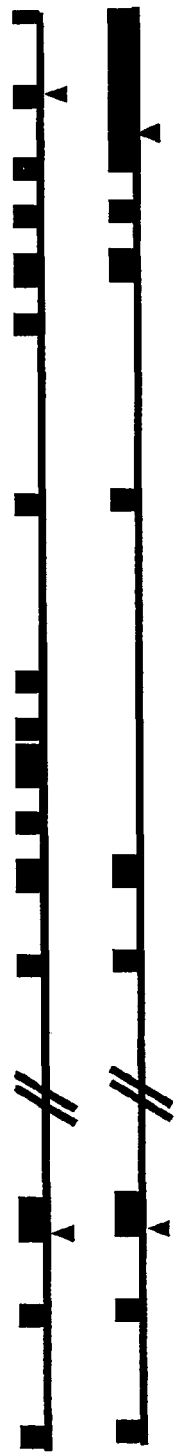

Next another gene, A5736, also markedly up-regulated in more than 50% of prostate cancer was focused and validated the over-expressed pattern in prostate cancer cells by RT-PCR (FIG. 2A). This gene overlapped with MICAL2 (Molecule Interacting with CasL 2). Northern blot analysis using the sequence of A5736 as a probe demonstrated that a transcript of approximately 7.5 kb was abundantly expressed in testis and prostate cancer cell lines. However, normal transcript of MICAL2 transcript was confirmed to have a size of 3.8 kb (FIG. 2B). To solve this discrepancy of size, RACE was performed to identify unknown transcribed region. As a result of RACE using testis cDNA, novel variants of MICAL2 with a size of 7.5 kb were identified. The coding region of the 3' terminus of the identified variants was different from MICAL2 and encoded a 976 amino-acid residue instead of the 1124 amino-acid residue of the normal MICAL2 protein (FIG. 2C). According to the invention, the present inventors discovered two novel variants of MICAL2, one long form variant (Accession number: AB 110785) and one short form variant (Accession number: AB110786) wherein one exon is spliced out from the long form variant. Herein, the variants are collectively called "MICAL2-PV (MICAL2prostate cancer-variants)".

(2) Subcellular Localization

Figure 3:
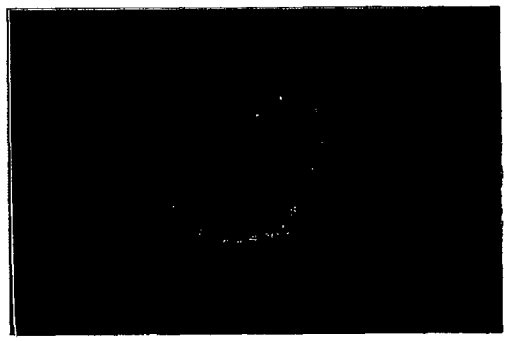
FIG. 3 depicts photographs showing the sublocalization of exogenous PCOTH protein (A) and MICAL2-PV protein (B) in COS7 cells. Exogenous PCOTH protein was localized in the cell membrane, while exogenous MICAL2-PV protein was localized in the cytoplasm of COS7 cells.
Figure 3:

To further investigate the subcellular localization of PCOTH and MICAL2-PV proteins, these proteins were ligated with tag and were transiently over-expressed in COS7 cells to perform immunocytochemical staining. As shown in FIG. 3, exogenous PCOTH-HA protein was localized in the cell membrane or submembrane (FIG. 3A), and exogenous MICAL2-PV-Myc protein was localized in the cytoplasma of COS7 cells (FIG. 3B).

(3) Growth Suppression Mediated by siRNA in Prostate Cancer Cell Lines

Figure 4:
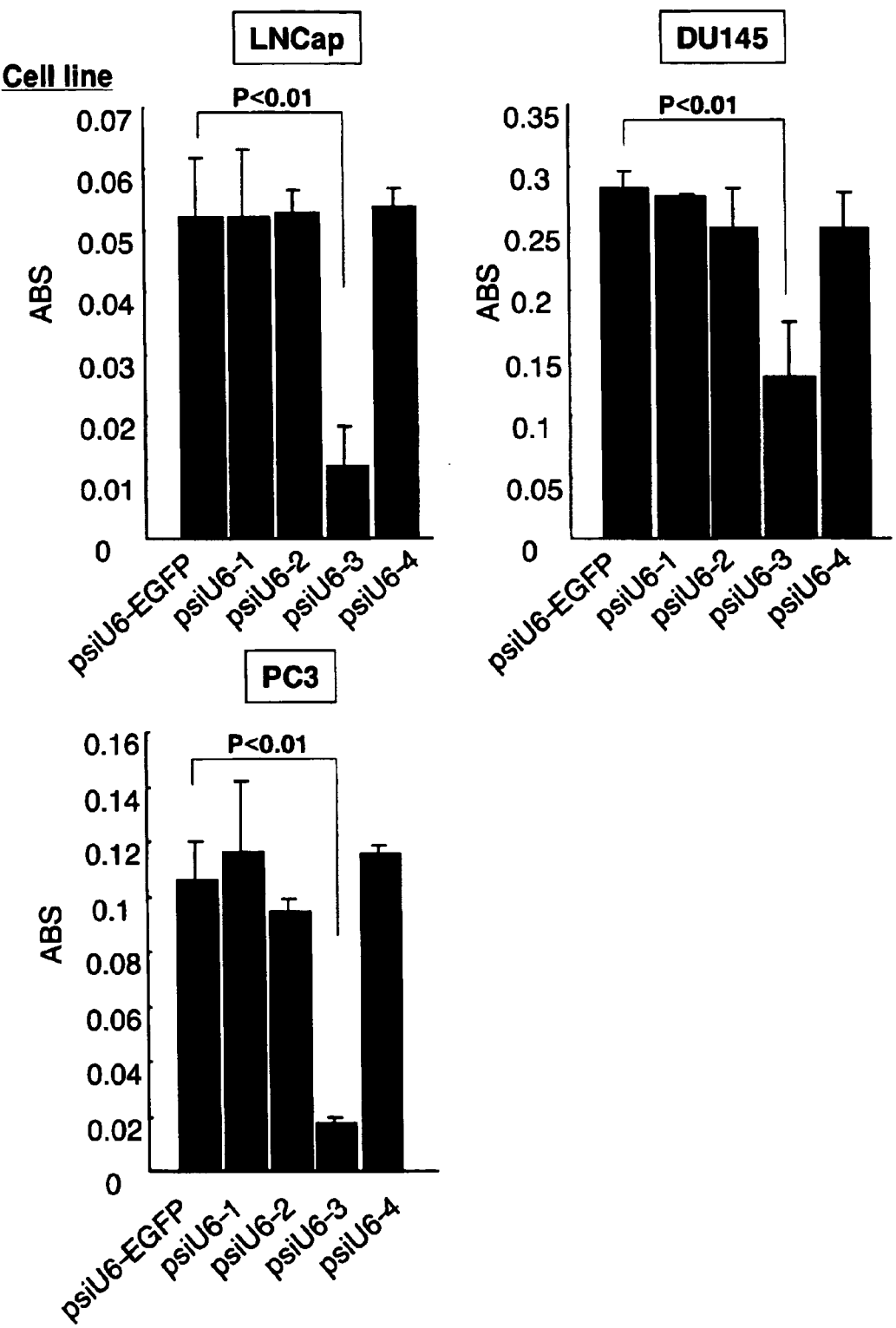
FIG. 4(A) depicts photographs showing the effect of knocking-down PCOTH in prostate cancer cell line using siRNA. Several U6-promoter-siRNA constructs (sil-4 targeting PCOTH and one targeting EGFP) were transfected to PC3. The result of RT-PCR demonstrated that a drastic effect is achieved by knocking-down PCOTH in PC3 cells transfected with si3. (B) depicts a photograph showing the result of colony formation assay in PC3 after the transfection with U6-promoter-siRNA constructs. The number of colonies was concordant with the knocking-down effect of si3 on PCOTH. (C) depicts the result of MTT assay in three prostate cancer cell lines (LNCaP, DU145 and PC3) after knocking-down PCOTH with siRNA. The cell growth of cells was also concordant with the knocking-down effect of si3 on PCOTH. (D) depicts photographs showing the effect of knocking-down MICAL2-PV in prostate cancer cell line with siRNA. Several U6-promoter-siRNA constructs (sil-3 targeting MICAL2-PV and one targeting EGFP) were transfected into PC3. The result of RT-PCR showed a drastic effect of knocking-down PCOTH in PC3 cells by the transfection with si2. (E) depicts photographs showing the result of colony formation assay on PC3 after the transfection with U6-promoter-siRNA constructs. The number of colonies was concordant with the knocking-down effect of si2 on MICAL2-PV.
Figure 4:
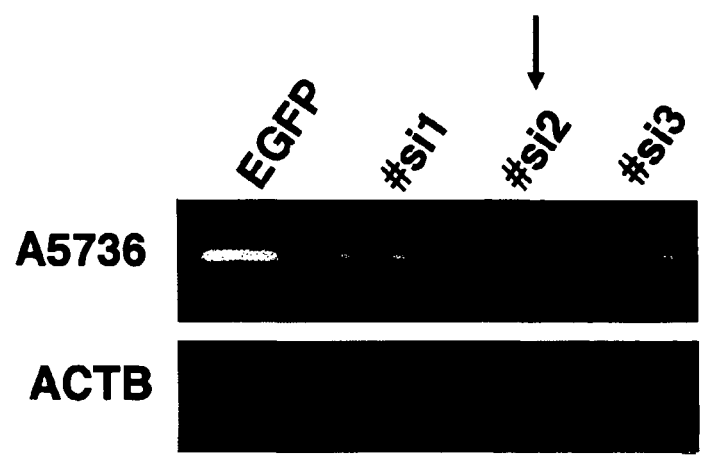
Figure 4:
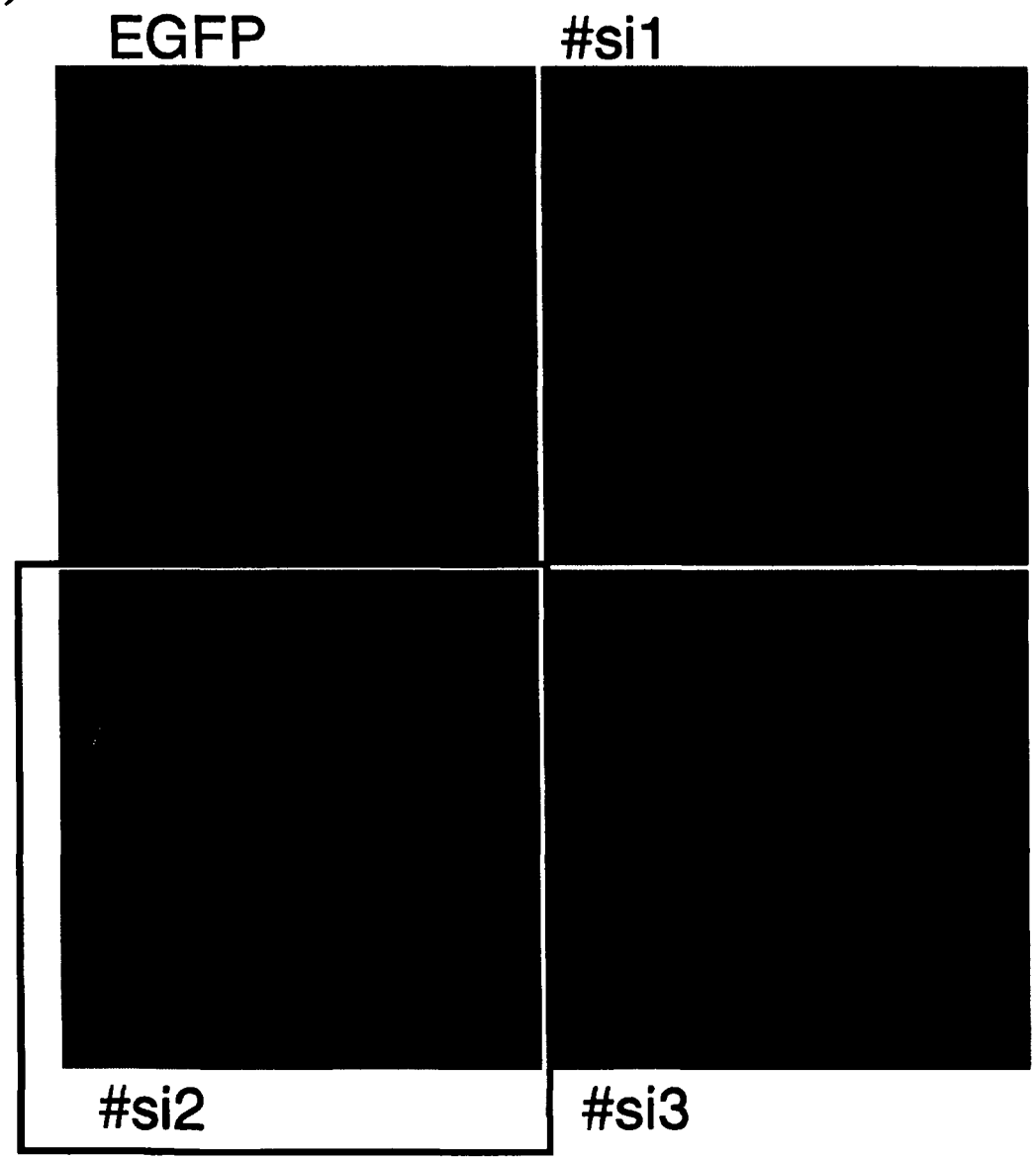

To investigate the effect of over-expression of these genes on the growth or survival of prostate cancer cells, endogenous expression of these genes were specifically knocked down by the mammalian vector-based RNA interference (RNAi) technique. Transfection of siRNA-producing vectors of some of the designed siRNA for PCOTH (FIG. 4A) and MICAL2-PV (FIG. 4D) resulted in reduction of endogenous expression. The knocking-down effect by the siRNA on the transcript of PCOTH resulted in a drastic growth suppression in the colony formation assay and MTT assay (FIGS. 4B and 4C). The knocking-down effect by the siRNA on the transcript of MICAL2-PV also resulted in growth suppression in the colony formation assay (FIG. 4E). These findings strongly suggest that over-expression of PCOTH and MICAL2-PV in prostate cancer cells is associated with cancer cell growth and that these genes or proteins encoded by the genes are promising molecular targets for prostate cancer therapy wherein the genes are blocked or knocked down.

INDUSTRIAL APPLICABILITY

The expression of human genes MICAL2-PV and PCOTH is markedly elevated in prostate cancer as compared to non-cancerous prostate duct epithelium. Accordingly, these genes may serve as a diagnostic marker of prostate cancer and the proteins encoded thereby may be used in diagnostic assays of prostate cancer.

The present inventors have also shown that the expression of novel protein MICAL2-PV or PCOTH promotes cell growth whereas cell growth is suppressed by small interfering RNAs corresponding to the MICAL2-PV or PCOTH gene. These findings suggest that each of MICAL2-PV and PCOTH proteins stimulate oncogenic activity. Thus, each of these novel oncoproteins is a useful target for the development of anti-cancer pharmaceuticals. For example, agents that block the expression of MICAL2-PV or PCOTH, or prevent its activity may find therapeutic utility as anti-cancer agents, particularly anti-cancer agents for the treatment of prostate cancers. Examples of such agents include antisense oligonucleotides, small interfering RNAs, and ribozymes against the MICAL2-PV or PCOTH gene, and antibodies that recognize MICAL2-PV or PCOTH.

While the invention has been described in detail and with reference to specific embodiments thereof, it will be apparent to one skilled in the art that various changes and modifications can be made therein without departing from the spirit and scope of the invention.

The invention claimed is:

1. A substantially pure polypeptide comprising the entirety of the amino acid sequence of SEQ ID NO: 4.

2. A method for producing the polypeptide of claim 1, said method comprising the steps of:

(a) culturing a host cell comprising:

(1) a polynucleotide encoding the polypeptide; or
(2) a vector comprising the polynucleotide encoding the polypeptide;

(b) allowing the host cell to express the polypeptide; and
(c) collecting the expressed polypeptide.

* * * * *

SEQUENCE LISTING

```
<160> NUMBER OF SEQ ID NOS: 28

<210> SEQ ID NO 1
<211> LENGTH: 826
<212> TYPE: DNA
<213> ORGANISM: Homo sapiens
<220> FEATURE:
<221> NAME/KEY: CDS
<222> LOCATION: (332)..(634)
<223> OTHER INFORMATION:

<400> SEQUENCE: 1 aagggctca tgcagaagca gttcccggac ccgacactct gggtaggaga ccactaaacc      60
cggcccctca aagcagaggt gaccttgccc tcatcgagag cgcacacaag acgccactgt     120
aaaaggatca cagatggaga gacattttgc cacacgatga atcacacacc acatctcatc     180
cccgagcttc agctgcagga caatgctgcc agaggcctgg tcctcagagc tcacgtaagc     240
```

-continued

```
atctctggtg tgcagtattt ttactccgtt tttgaccaaa gacacctgaa cattcctgga          300
gaaaacagtg atgtggatct tatcaaattt a atg ggc aca tct gaa gaa gga            352
                                   Met Gly Thr Ser Glu Glu Gly
                                   1               5 aac ttg ctc agc acc gtg agc ccc aca gtg aaa gca ctt ttt ggc aag           400
Asn Leu Leu Ser Thr Val Ser Pro Thr Val Lys Ala Leu Phe Gly Lys
        10                  15                  20 act aga gtc tca ccg att ttc cct ttc tct cct cga tct cct ttc cag           448
Thr Arg Val Ser Pro Ile Phe Pro Phe Ser Pro Arg Ser Pro Phe Gln
 25                  30                  35 cct ctt att ccc cgg act cct ggc tca ccc tgg ggc ccc gtg ggt cca           496
Pro Leu Ile Pro Arg Thr Pro Gly Ser Pro Trp Gly Pro Val Gly Pro
40                  45                  50                  55 gct tct ccc ttg gga cca ggc ttt cca ata ggg ccc atg ggg ccc ggt           544
Ala Ser Pro Leu Gly Pro Gly Phe Pro Ile Gly Pro Met Gly Pro Gly
                60                  65                  70 aaa cca gtt ggg ccc aaa ggc cca atg ttg ccc ctt ggc ccc tca gga           592
Lys Pro Val Gly Pro Lys Gly Pro Met Leu Pro Leu Gly Pro Ser Gly
        75                  80                  85 cca gtg gga ccc acg tca ccc tta ttc ccc ttc tgc ccc tga                   634
Pro Val Gly Pro Thr Ser Pro Leu Phe Pro Phe Cys Pro
 90                  95                 100 ggcccagtct ctcctcggag gcctttctct cccatgggcc ctgcaagccc cttggggcca          694
tgttttcctg gggatcctct tgagccttga tcacctttga tgcctttgc ttcaactttt          754 ccatctgctc ctaaatagag aaagagcaaa taaagagata gtttgtgaaa gataaaaaaa          814
aaaaaaaaaa aa                                                             826

<210> SEQ ID NO 2
<211> LENGTH: 100
<212> TYPE: PRT
<213> ORGANISM: Homo sapiens

<400> SEQUENCE: 2

Met Gly Thr Ser Glu Glu Gly Asn Leu Leu Ser Thr Val Ser Pro Thr
1               5                   10                  15

Val Lys Ala Leu Phe Gly Lys Thr Arg Val Ser Pro Ile Phe Pro Phe
            20                  25                  30

Ser Pro Arg Ser Pro Phe Gln Pro Leu Ile Pro Arg Thr Pro Gly Ser
        35                  40                  45

Pro Trp Gly Pro Val Gly Pro Ala Ser Pro Leu Gly Pro Gly Phe Pro
    50                  55                  60

Ile Gly Pro Met Gly Pro Gly Lys Pro Val Gly Pro Lys Gly Pro Met
65                  70                  75                  80

Leu Pro Leu Gly Pro Ser Gly Pro Val Gly Pro Thr Ser Pro Leu Phe
                85                  90                  95

Pro Phe Cys Pro
            100

<210> SEQ ID NO 3
<211> LENGTH: 6805
<212> TYPE: DNA
<213> ORGANISM: Homo sapiens
<220> FEATURE:
<221> NAME/KEY: CDS
<222> LOCATION: (265)..(3195)
<223> OTHER INFORMATION:

<400> SEQUENCE: 3
```

-continued

```
ccgggccgcc tcgctcgctc ccagctctgt cagtggcccg cggggcccga tcgctgcgcc      60
cgcggccagg gccgaggcag gcctgacccg ggccgggca gcccgcgcga ctttcggaac      120
atggcaaccc gtgtgtgtct catcccagaa agagaagact ttaaccactg tgatgcctga     180
gaatccagtg tgacgtttct ccagatactt catgctgttc acctgtgtcc tcgccgcacc     240
actgccgcac acgactcctg aacc atg ggg gaa aac gag gat gag aag cag       291
                           Met Gly Glu Asn Glu Asp Glu Lys Gln
                             1               5 gcc cag gcg ggg cag gtt ttt gag aac ttt gtc cag gca tcc acg tgc       339
Ala Gln Ala Gly Gln Val Phe Glu Asn Phe Val Gln Ala Ser Thr Cys
 10              15                  20                  25 aaa ggt acc ctc cag gcc ttc aac att ctc aca cga cac ctg gac cta       387
Lys Gly Thr Leu Gln Ala Phe Asn Ile Leu Thr Arg His Leu Asp Leu
             30                  35                  40 gac cct ctg gac cac aga aac ttt tat tcc aag ctc aag tcc aag gtg       435
Asp Pro Leu Asp His Arg Asn Phe Tyr Ser Lys Leu Lys Ser Lys Val
                 45                  50                  55 acc acc tgg aaa gcc aaa gcc ctg tgg tac aaa ttg gat aag cgt ggt       483
Thr Thr Trp Lys Ala Lys Ala Leu Trp Tyr Lys Leu Asp Lys Arg Gly
 60                  65                  70 tcc cac aaa gag tat aag cga ggg aag tcg tgc acg aac acc aag tgt       531
Ser His Lys Glu Tyr Lys Arg Gly Lys Ser Cys Thr Asn Thr Lys Cys
 75                  80                  85 ctc ata gtt ggg gga gga ccc tgt ggc ttg cgc act gcc att gaa ctt       579
Leu Ile Val Gly Gly Gly Pro Cys Gly Leu Arg Thr Ala Ile Glu Leu
 90                  95                 100                 105 gcc tac ctg gga gcc aaa gtg gtc gtg gtg gag aag agg gac tcc ttc       627
Ala Tyr Leu Gly Ala Lys Val Val Val Val Glu Lys Arg Asp Ser Phe
                110                 115                 120 tcc cgg aac aac gtg cta cac ctc tgg cct ttc acc atc cat gac ctt       675
Ser Arg Asn Asn Val Leu His Leu Trp Pro Phe Thr Ile His Asp Leu
                125                 130                 135 cgg ggc ctg gga gcc aag aag ttc tat ggg aag ttc tgt gct ggc tcc       723
Arg Gly Leu Gly Ala Lys Lys Phe Tyr Gly Lys Phe Cys Ala Gly Ser
                140                 145                 150 atc gac cat atc agt att cgc caa cta cag ctc atc cta ttc aag gtg       771
Ile Asp His Ile Ser Ile Arg Gln Leu Gln Leu Ile Leu Phe Lys Val
155                 160                 165 gcc ctg atg ctg gga gtt gaa atc cat gtg aat gtg gag ttc gtg aag       819
Ala Leu Met Leu Gly Val Glu Ile His Val Asn Val Glu Phe Val Lys
170                 175                 180                 185 gtt cta gag cct cct gaa gat caa gaa aat caa aaa att ggc tgg cgg       867
Val Leu Glu Pro Pro Glu Asp Gln Glu Asn Gln Lys Ile Gly Trp Arg
                190                 195                 200 gca gaa ttt ctc cct aca gac cat tct ctg tcg gag ttt gag ttt gac       915
Ala Glu Phe Leu Pro Thr Asp His Ser Leu Ser Glu Phe Glu Phe Asp
                205                 210                 215 gtc atc att ggt gcc gat ggc cgc agg aac acc ctg gaa ggg ttc aga       963
Val Ile Ile Gly Ala Asp Gly Arg Arg Asn Thr Leu Glu Gly Phe Arg
                220                 225                 230 aga aaa gaa ttc cgt ggg aag ctg gcg att gcc atc acc gcc aac ttc      1011
Arg Lys Glu Phe Arg Gly Lys Leu Ala Ile Ala Ile Thr Ala Asn Phe
235                 240                 245 ata aac aga aac agc aca gcg gaa gcc aag gtg gaa gag att agt ggt      1059
Ile Asn Arg Asn Ser Thr Ala Glu Ala Lys Val Glu Glu Ile Ser Gly
250                 255                 260                 265 gtg gct ttc atc ttc aat cag aaa ttt ttt cag gac ctt aaa gaa gaa      1107
Val Ala Phe Ile Phe Asn Gln Lys Phe Phe Gln Asp Leu Lys Glu Glu
```

-continued

```
                    270                 275                 280
aca ggc ata gat ctt gag aac att gtt tac tac aag gac tgc acc cac       1155
Thr Gly Ile Asp Leu Glu Asn Ile Val Tyr Tyr Lys Asp Cys Thr His
            285                 290                 295 tat ttt gta atg aca gcc aag aag cag agc ctg ctc gac aaa ggt gtc       1203
Tyr Phe Val Met Thr Ala Lys Lys Gln Ser Leu Leu Asp Lys Gly Val
        300                 305                 310 atc att aac gac tac atc gac aca gag atg ctg ctg tgt gcg gag aac       1251
Ile Ile Asn Asp Tyr Ile Asp Thr Glu Met Leu Leu Cys Ala Glu Asn
315                 320                 325 gtg aac caa gac aac ctg cta tcc tat gcc cgg gaa gct gca gac ttt       1299
Val Asn Gln Asp Asn Leu Leu Ser Tyr Ala Arg Glu Ala Ala Asp Phe
330                 335                 340                 345 gcc acc aac tac cag ctg cca tcc tta gac ttt gcc atg aac cac tat       1347
Ala Thr Asn Tyr Gln Leu Pro Ser Leu Asp Phe Ala Met Asn His Tyr
            350                 355                 360 ggg cag cct gat gtg gcc atg ttt gac ttt acc tgc atg tat gcc tca       1395
Gly Gln Pro Asp Val Ala Met Phe Asp Phe Thr Cys Met Tyr Ala Ser
        365                 370                 375 gag aac gcg gcc ctg gtg cgg gag cgg cag gcg cac cag ctc ctc gtg       1443
Glu Asn Ala Ala Leu Val Arg Glu Arg Gln Ala His Gln Leu Leu Val
    380                 385                 390 gcc ctt gtg ggt gac agc ttg ctt gag cca ttt tgg ccc atg ggt aca       1491
Ala Leu Val Gly Asp Ser Leu Leu Glu Pro Phe Trp Pro Met Gly Thr
395                 400                 405 ggc tgt gcc cgt ggc ttc ctg gca gcc ttt gac acg gca tgg atg gtg       1539
Gly Cys Ala Arg Gly Phe Leu Ala Ala Phe Asp Thr Ala Trp Met Val
410                 415                 420                 425 aag agc tgg aac cag ggc acc cct ccc ctg gag ctg ctg gct gaa agg       1587
Lys Ser Trp Asn Gln Gly Thr Pro Pro Leu Glu Leu Leu Ala Glu Arg
            430                 435                 440 gaa agt ctc tac cgg ctg tta cct cag aca acc ccg gag aac atc aac       1635
Glu Ser Leu Tyr Arg Leu Leu Pro Gln Thr Thr Pro Glu Asn Ile Asn
        445                 450                 455 aag aac ttt gag cag tac acg ttg gac cca ggg aca cgg tac cca aac       1683
Lys Asn Phe Glu Gln Tyr Thr Leu Asp Pro Gly Thr Arg Tyr Pro Asn
    460                 465                 470 ctc aac tca cac tgt gtc agg ccc cat cag gtg aag cat ttg tat atc       1731
Leu Asn Ser His Cys Val Arg Pro His Gln Val Lys His Leu Tyr Ile
475                 480                 485 act aag gag ctg gag cac tac cct ctc gag aga ctg ggc tcg gtg agg       1779
Thr Lys Glu Leu Glu His Tyr Pro Leu Glu Arg Leu Gly Ser Val Arg
490                 495                 500                 505 aga tct gtc aac ctc tcc agg aag gag tca gat atc cgg ccc agc aag       1827
Arg Ser Val Asn Leu Ser Arg Lys Glu Ser Asp Ile Arg Pro Ser Lys
            510                 515                 520 ctc ctg acc tgg tgc cag cag cag aca gag ggc tac cag cat gtc aac       1875
Leu Leu Thr Trp Cys Gln Gln Gln Thr Glu Gly Tyr Gln His Val Asn
        525                 530                 535 gtc acc gac ctg acc aca tcc tgg cgc agt ggg ttg gcc ctg tgt gcc       1923
Val Thr Asp Leu Thr Thr Ser Trp Arg Ser Gly Leu Ala Leu Cys Ala
    540                 545                 550 atc atc cac cgc ttc cgg cct gag ctc atc aac ttt gac tct ttg aat       1971
Ile Ile His Arg Phe Arg Pro Glu Leu Ile Asn Phe Asp Ser Leu Asn
555                 560                 565 gaa gat gat gct gtg gag aac aac cag ctc gca ttt gat gtg gcc gag       2019
Glu Asp Asp Ala Val Glu Asn Asn Gln Leu Ala Phe Asp Val Ala Glu
570                 575                 580                 585 cga gag ttt ggg atc cct cca gtg acc acg ggc aaa gag atg gca tct       2067
```

```
                Arg Glu Phe Gly Ile Pro Pro Val Thr Thr Gly Lys Glu Met Ala Ser
                                590                 595                 600 gcc cag gag cct gac aag ctc agc atg gtc atg tac ctc tcc aag ttc         2115
Ala Gln Glu Pro Asp Lys Leu Ser Met Val Met Tyr Leu Ser Lys Phe
                605                 610                 615 tac gag ctc ttc cgg ggc acc cca ctg agg ccc gtg gat tct tgg cgc         2163
Tyr Glu Leu Phe Arg Gly Thr Pro Leu Arg Pro Val Asp Ser Trp Arg
                620                 625                 630 aaa aac tat gga gaa aat gct gac ctc agc ttg gcc aaa tca tcc att         2211
Lys Asn Tyr Gly Glu Asn Ala Asp Leu Ser Leu Ala Lys Ser Ser Ile
635                 640                 645 tct aat aac tat ctc aac ctc aca ttt cca agg aag agg act cca cgg         2259
Ser Asn Asn Tyr Leu Asn Leu Thr Phe Pro Arg Lys Arg Thr Pro Arg
650                 655                 660                 665 gtg gat ggt caa acc gga gag aat gac atg aac aaa cgg aga cgg aag         2307
Val Asp Gly Gln Thr Gly Glu Asn Asp Met Asn Lys Arg Arg Arg Lys
                670                 675                 680 ggc ttc acc aac ctg gac gag cct tca aac ttt tcc agc cgt agc ttg         2355
Gly Phe Thr Asn Leu Asp Glu Pro Ser Asn Phe Ser Ser Arg Ser Leu
                685                 690                 695 ggc tcc aat caa gag tgt ggg agc agt aag gaa ggt gga aat cag aac         2403
Gly Ser Asn Gln Glu Cys Gly Ser Ser Lys Glu Gly Gly Asn Gln Asn
700                 705                 710 aaa gtc aag tcc atg gcg aat cag ctg ctg gcc aag ttt gag gag agc         2451
Lys Val Lys Ser Met Ala Asn Gln Leu Leu Ala Lys Phe Glu Glu Ser
                715                 720                 725 act cgg aac ccc tca ctc atg aag cag gaa aag aag tca cct tca ggg         2499
Thr Arg Asn Pro Ser Leu Met Lys Gln Glu Lys Lys Ser Pro Ser Gly
730                 735                 740                 745 ttc cat ttt cat ccc agc cat ttg aga aca gtg cat cct cag gaa tct         2547
Phe His Phe His Pro Ser His Leu Arg Thr Val His Pro Gln Glu Ser
                750                 755                 760 atg cga aag tca ttt ccc ctt aac ctg gga ggc agc gac acg tgt tac         2595
Met Arg Lys Ser Phe Pro Leu Asn Leu Gly Gly Ser Asp Thr Cys Tyr
                765                 770                 775 ttc tgt aag aaa cgt gtg tac gtg atg gaa cgg ctg agc gcc gag ggc         2643
Phe Cys Lys Lys Arg Val Tyr Val Met Glu Arg Leu Ser Ala Glu Gly
                780                 785                 790 cac ttc ttc cac cgg gag tgt ttc cgc tgc agc atc tgt gcc acc acc         2691
His Phe Phe His Arg Glu Cys Phe Arg Cys Ser Ile Cys Ala Thr Thr
                795                 800                 805 ttg cgc ctg gcc gcc tac acc ttt gac tgc gat gaa ggc aaa ttt tac         2739
Leu Arg Leu Ala Ala Tyr Thr Phe Asp Cys Asp Glu Gly Lys Phe Tyr
810                 815                 820                 825 tgc aag cct cac ttc att cac tgt aaa acc aat agc aaa caa cgg aag         2787
Cys Lys Pro His Phe Ile His Cys Lys Thr Asn Ser Lys Gln Arg Lys
                830                 835                 840 aga cgg gca gag ttg aag caa caa aga gag gag gag gca aca tgg caa         2835
Arg Arg Ala Glu Leu Lys Gln Gln Arg Glu Glu Glu Ala Thr Trp Gln
                845                 850                 855 gag cag gaa gcc cct cgg aga gac act ccc acc gaa agt tct tgc gca         2883
Glu Gln Glu Ala Pro Arg Arg Asp Thr Pro Thr Glu Ser Ser Cys Ala
                860                 865                 870 gtg gcc gcc att ggc acc ctg gaa ggc agc ccc cca ggt atc tcc acc         2931
Val Ala Ala Ile Gly Thr Leu Glu Gly Ser Pro Pro Gly Ile Ser Thr
875                 880                 885 tcc ttc ttt agg aag gtg ctg ggc tgg ccc ctc agg ctg ccg agg gac         2979
Ser Phe Phe Arg Lys Val Leu Gly Trp Pro Leu Arg Leu Pro Arg Asp
890                 895                 900                 905
```

```
ctg tgt aac tgg atg cag gga ctc ctg caa gct gct ggc ctc cat atc      3027
Leu Cys Asn Trp Met Gln Gly Leu Leu Gln Ala Ala Gly Leu His Ile
            910                 915                 920 agg gac aat gct tac aac tac tgc tac atg tac gag ctc ctg agc ctg      3075
Arg Asp Asn Ala Tyr Asn Tyr Cys Tyr Met Tyr Glu Leu Leu Ser Leu
        925                 930                 935 ggg ctg cca ctc ctc tgg gcg ttc tct gag gtc ctg gca gcc atg tac      3123
Gly Leu Pro Leu Leu Trp Ala Phe Ser Glu Val Leu Ala Ala Met Tyr
    940                 945                 950 agg gaa tct gag ggc tcc ctc gag agc atc tgc aac tgg gtg ctc agg      3171
Arg Glu Ser Glu Gly Ser Leu Glu Ser Ile Cys Asn Trp Val Leu Arg
955                 960                 965 tgc ttc cca gtc aag ctc cgc tga catggctggc tgccccaaag tgccttcaca    3225
Cys Phe Pro Val Lys Leu Arg
970             975 tttccaggga ggcttcagat ggcagtgcgt ttgcagtttg ctcaggctct ggccaggaag    3285
cctagcattc tctaagcaat tagctcaaag ccaaagaatt tcacatgggc acctccgcc     3345 tggccttatc agggtgaaca tctactcacg gtgctagggc agggatgat atgaaggatc     3405 ttttctatag ctttgtgagc catacttctg gtttacatt tcaatttttt taattttaat    3465
tagcccagag aaagcatttt tttctatgag tgtcaatttt tctaaacatg gtttgaagc    3525 ttataaccag tttataaac cccttgaaca ctgcagtgag ttatcaaagc cactgcctgc    3585
aaagtggatg atttaagatt ttacacgcat gaaaatgagt gtgccatctc ctgaccagtg    3645 cctttttgact taggtaccca gatgccactt gtcagcagca ggatacttt tacaacacga    3705 aagcataatt attttagaag aagagagtag aagggcagaa tagaattcaa cttacagaag    3765
cacggagcag tgtgtggttg ctgttatct gtcccctgg gaggaggact gttttgctcc     3825
cttgttttga tgttaaacag tagcttaaag ctttccccc ccataccaac tcacagccaa     3885
atgacaaaga accgtggggt ttcaacagat tctacaaaca tgcatttcc cttcccacta    3945 atgggcactg cagggaaagc ccattggcat ttgaccatgg agctgatgca gtgccaaaga    4005
tgagctcttt caactgatgg cattttagcc cctgtggctc ccagcggatc ccccagcccg    4065
ggctgcaggc tgagccaagg ctgtgcaggg tccatattgg tcaggccaag tggagtggaa    4125
gactctgtcc acttatgtgg tgtcctttgg gactgagggg gtttgttagc acatcaggct    4185
attgctggga agcgtggcct gcccagtgag cattgcctgt ggacatcctg actgcttagc    4245
tgctccgctg ccacacatat gtggtcaaaa cagaaaccaa tttcacactg ccctgggaaa    4305
ggaatgggtc tgacctccag gggaagctct accatatctt gactggcagg gaaggctggg    4365
agtggaagct atttatggac tgatccaaag gacatatgca tgagtaaggg taaaaatgag    4425
catgcaggtc cacctgtgtt cttactctgg gtatctagaa gagtcctcag ctctccctac    4485
tccacgctgc ctagacatac acagctgcag gtctggctg aacaatcaag gggccgccag     4545
agaaaggcca tctacggtgc gcagtgtatc tggagttgct gggcccaaga tagctctgtg    4605
gagttatcac tagagatgcc tctggattaa ctaagaggtg tgcctgggtg tgggtgagga    4665
gtcagaacct tgagagctt tgagatgaca gtttctatgg ggcgggaaga aggaggtgca     4725
tttctacaaa cacttccctg aaatccttgg gaaaaacaga ggcatggccg tggccaactc    4785
tgtgggaact ggcgcctctg tccttgttgg cactgttctc agtccgatga cttgcattgt    4845
gttttctcca atttttgctg ggattttaat gttcagcatg gtgggaggaa cccttgattc    4905
cttttgtttg agtatagaaa gtaaattttt gaggtcatga tgtgaacggc catgttattg    4965
tgattatctt cagctcagga taggctgaga tgctttgtgg agtgttccat gaagcccgag    5025
```

-continued

```
tcggaatctc tgactgtcgt gtacagccat aaggagactg gtttgaatta ctgtggcgag    5085
acagggcgtg cctgtcagaa atctgagatg tttgtacgct ctgagatgtt gaacctttct    5145
ggtgggcagc accgacaccc aggggtggac ccccgaggat gaatgcctct aggcctccgc    5205
aacatattca agaatgaatg ggagacgcta gagtaaaatg ggggcagaga ggatatcagg    5265
gagcaagatg caaactgtgt gcatccactc tcgtaaacaa gtagctggtc acaaccagaa    5325
aggttcatct ctcctaagca aacagcgact cttcagagg aagtttccct ctttcaatcg     5385
tggccttatt ttcaactccg gtgccttctc gtgatgttaa tcatttcctt ttttccccac    5445
actaagctct cttttctatc tttctctctc tttccaatct tacgccatgg ccatcagttc    5505
atttcagcct tccagtgcta cacccacttc ttggctgaca cacttctgct ctaaggtgac    5565
tggttttctt gccaattttc aaagagtggt actaaccccc aacccgcttt ccgcaccccg    5625
tcctctccgc cagcagtact ggttgcacta actgtgagtg tcttgcatac tgatggactc    5685
atttggtggc atggttggct aacagcatgg cggggggtgt tcagcttgag acccatgcct    5745
gtgttcattt cccatggagc tggcagcctg gtctacccca agtgcatgcc ccgcctctcc    5805
tctctcccct gggtctgcct gcgtgcatgc ttctccagtt gcgtctgcga agctacctac    5865
tttcttggga gggtcgacct tgatcatgaa acaataccat gagggggcct ctgtcacctt    5925
tgaaaagaac acttttgag cagcctcaaa aagctcatac ataccagcgc cttcttaaat     5985
tggctctaat gtaaagattg ttaatgtcat ttatcaaaac cataggtgat tatttggagg    6045
gatttaaaaa acttaattac tctcaggcct catcccaagc ttgacacatg ctctgtaggt    6105
tgaacacata atcacaaata ttctagcaaa tgctgccttg gttgcagcct gcactgtaga    6165
cccaagggtt ttgctgtggc tcttcttatc tcccttggct cataaagccc cagatgatgc    6225
cagagcttca attagagcca tcatcatccc aggcagggat atctttgaga aatgactcag    6285
ttcagcccca ggcccctgtg actctgctta aagcacacat ttctgctgac tcttgtacct    6345
ggggcagcag gataatcacc aacacactct taacgagaaa caacacacca agcaccgtgg    6405
agctgtccta ggcaacactc gcggtctcag gctgcggtgg gcgtctgtcc tgcatgtggc    6465
ccagaccacc ctgaccccg gcctgcctg cctggccctg catgctgcac gctcactgta     6525
tttgtgcaga tcctgccag tacaaagtcg ttgctcttgt cttatcttct cttacagagt    6585
ctccctccct ttatagaatg tcaaccaaag agtgccctcc tcccctctca gcctcctctt    6645
tagctagcct cccatctca tcacaacgca tgtctgtgac ctttggtaat catttacagt     6705
gccacacgga accctgtatt ttgcacacag caaaacaaac aatgtttagc tttatttatg    6765
gtatttgatg ctgtaaatgg aaataaatat tgttctttat                          6805
```

<210> SEQ ID NO 4
<211> LENGTH: 976
<212> TYPE: PRT
<213> ORGANISM: Homo sapiens

<400> SEQUENCE: 4

```
Met Gly Glu Asn Glu Asp Glu Lys Gln Ala Gln Ala Gly Gln Val Phe
1               5                   10                  15

Glu Asn Phe Val Gln Ala Ser Thr Cys Lys Gly Thr Leu Gln Ala Phe
            20                  25                  30

Asn Ile Leu Thr Arg His Leu Asp Leu Asp Pro Leu Asp His Arg Asn
        35                  40                  45

Phe Tyr Ser Lys Leu Lys Ser Lys Val Thr Thr Trp Lys Ala Lys Ala
```

-continued

```
                 50                  55                  60
Leu Trp Tyr Lys Leu Asp Lys Arg Gly Ser His Lys Glu Tyr Lys Arg
 65                  70                  75                  80

Gly Lys Ser Cys Thr Asn Thr Lys Cys Leu Ile Val Gly Gly Gly Pro
                 85                  90                  95

Cys Gly Leu Arg Thr Ala Ile Glu Leu Ala Tyr Leu Gly Ala Lys Val
                100                 105                 110

Val Val Val Glu Lys Arg Asp Ser Phe Ser Arg Asn Val Leu His
                115                 120                 125

Leu Trp Pro Phe Thr Ile His Asp Leu Arg Gly Leu Gly Ala Lys Lys
                130                 135                 140

Phe Tyr Gly Lys Phe Cys Ala Gly Ser Ile Asp His Ile Ser Ile Arg
145                 150                 155                 160

Gln Leu Gln Leu Ile Leu Phe Lys Val Ala Leu Met Leu Gly Val Glu
                165                 170                 175

Ile His Val Asn Val Glu Phe Val Lys Val Leu Glu Pro Pro Glu Asp
                180                 185                 190

Gln Glu Asn Gln Lys Ile Gly Trp Arg Ala Glu Phe Leu Pro Thr Asp
                195                 200                 205

His Ser Leu Ser Glu Phe Glu Phe Asp Val Ile Ile Gly Ala Asp Gly
                210                 215                 220

Arg Arg Asn Thr Leu Glu Gly Phe Arg Arg Lys Glu Phe Arg Gly Lys
225                 230                 235                 240

Leu Ala Ile Ala Ile Thr Ala Asn Phe Ile Asn Arg Asn Ser Thr Ala
                245                 250                 255

Glu Ala Lys Val Glu Glu Ile Ser Gly Val Ala Phe Ile Phe Asn Gln
                260                 265                 270

Lys Phe Phe Gln Asp Leu Lys Glu Glu Thr Gly Ile Asp Leu Glu Asn
                275                 280                 285

Ile Val Tyr Tyr Lys Asp Cys Thr His Tyr Phe Val Met Thr Ala Lys
                290                 295                 300

Lys Gln Ser Leu Leu Asp Lys Gly Val Ile Ile Asn Asp Tyr Ile Asp
305                 310                 315                 320

Thr Glu Met Leu Leu Cys Ala Glu Asn Val Asn Gln Asp Asn Leu Leu
                325                 330                 335

Ser Tyr Ala Arg Glu Ala Ala Asp Phe Ala Thr Asn Tyr Gln Leu Pro
                340                 345                 350

Ser Leu Asp Phe Ala Met Asn His Tyr Gly Gln Pro Asp Val Ala Met
                355                 360                 365

Phe Asp Phe Thr Cys Met Tyr Ala Ser Glu Asn Ala Ala Leu Val Arg
                370                 375                 380

Glu Arg Gln Ala His Gln Leu Leu Val Ala Leu Val Gly Asp Ser Leu
385                 390                 395                 400

Leu Glu Pro Phe Trp Pro Met Gly Thr Gly Cys Ala Arg Gly Phe Leu
                405                 410                 415

Ala Ala Phe Asp Thr Ala Trp Met Val Lys Ser Trp Asn Gln Gly Thr
                420                 425                 430

Pro Pro Leu Glu Leu Leu Ala Glu Arg Glu Ser Leu Tyr Arg Leu Leu
                435                 440                 445

Pro Gln Thr Thr Pro Glu Asn Ile Asn Lys Asn Phe Glu Gln Tyr Thr
                450                 455                 460

Leu Asp Pro Gly Thr Arg Tyr Pro Asn Leu Asn Ser His Cys Val Arg
465                 470                 475                 480
```

```
Pro His Gln Val Lys His Leu Tyr Ile Thr Lys Glu Leu Glu His Tyr
            485                 490                 495
Pro Leu Glu Arg Leu Gly Ser Val Arg Ser Val Asn Leu Ser Arg
        500                 505             510
Lys Glu Ser Asp Ile Arg Pro Ser Lys Leu Leu Thr Trp Cys Gln Gln
        515                 520                 525
Gln Thr Glu Gly Tyr Gln His Val Asn Val Thr Asp Leu Thr Thr Ser
    530                 535                 540
Trp Arg Ser Gly Leu Ala Leu Cys Ala Ile Ile His Arg Phe Arg Pro
545                 550                 555                 560
Glu Leu Ile Asn Phe Asp Ser Leu Asn Glu Asp Asp Ala Val Glu Asn
                565                 570                 575
Asn Gln Leu Ala Phe Asp Val Ala Glu Arg Phe Gly Ile Pro Pro
            580                 585                 590
Val Thr Thr Gly Lys Glu Met Ala Ser Ala Gln Glu Pro Asp Lys Leu
        595                 600                 605
Ser Met Val Met Tyr Leu Ser Lys Phe Tyr Glu Leu Phe Arg Gly Thr
    610                 615                 620
Pro Leu Arg Pro Val Asp Ser Trp Arg Lys Asn Tyr Gly Glu Asn Ala
625                 630                 635                 640
Asp Leu Ser Leu Ala Lys Ser Ser Ile Ser Asn Asn Tyr Leu Asn Leu
                645                 650                 655
Thr Phe Pro Arg Lys Arg Thr Pro Arg Val Asp Gly Gln Thr Gly Glu
            660                 665                 670
Asn Asp Met Asn Lys Arg Arg Arg Lys Gly Phe Thr Asn Leu Asp Glu
        675                 680                 685
Pro Ser Asn Phe Ser Ser Arg Ser Leu Gly Ser Asn Gln Glu Cys Gly
    690                 695                 700
Ser Ser Lys Glu Gly Gly Asn Gln Asn Lys Val Lys Ser Met Ala Asn
705                 710                 715                 720
Gln Leu Leu Ala Lys Phe Glu Glu Ser Thr Arg Asn Pro Ser Leu Met
                725                 730                 735
Lys Gln Glu Lys Lys Ser Pro Ser Gly Phe His Phe His Pro Ser His
            740                 745                 750
Leu Arg Thr Val His Pro Gln Glu Ser Met Arg Lys Ser Phe Pro Leu
        755                 760                 765
Asn Leu Gly Gly Ser Asp Thr Cys Tyr Phe Cys Lys Lys Arg Val Tyr
    770                 775                 780
Val Met Glu Arg Leu Ser Ala Glu Gly His Phe Phe His Arg Glu Cys
785                 790                 795                 800
Phe Arg Cys Ser Ile Cys Ala Thr Thr Leu Arg Leu Ala Ala Tyr Thr
                805                 810                 815
Phe Asp Cys Asp Glu Gly Lys Phe Tyr Cys Lys Pro His Phe Ile His
            820                 825                 830
Cys Lys Thr Asn Ser Lys Gln Arg Lys Arg Ala Glu Leu Lys Gln
        835                 840                 845
Gln Arg Glu Glu Glu Ala Thr Trp Gln Glu Gln Ala Pro Arg Arg
    850                 855                 860
Asp Thr Pro Thr Glu Ser Ser Cys Ala Val Ala Ala Ile Gly Thr Leu
865                 870                 875                 880
Glu Gly Ser Pro Pro Gly Ile Ser Thr Ser Phe Phe Arg Lys Val Leu
                885                 890                 895
```

-continued

```
Gly Trp Pro Leu Arg Leu Pro Arg Asp Leu Cys Asn Trp Met Gln Gly
            900                 905                 910
Leu Leu Gln Ala Ala Gly Leu His Ile Arg Asp Asn Ala Tyr Asn Tyr
        915                 920                 925
Cys Tyr Met Tyr Glu Leu Leu Ser Leu Gly Leu Pro Leu Leu Trp Ala
    930                 935                 940
Phe Ser Glu Val Leu Ala Ala Met Tyr Arg Glu Ser Glu Gly Ser Leu
945                 950                 955                 960
Glu Ser Ile Cys Asn Trp Val Leu Arg Cys Phe Pro Val Lys Leu Arg
                965                 970                 975

<210> SEQ ID NO 5
<211> LENGTH: 6742
<212> TYPE: DNA
<213> ORGANISM: Homo sapiens
<220> FEATURE:
<221> NAME/KEY: CDS
<222> LOCATION: (265)..(3132)
<223> OTHER INFORMATION:

<400> SEQUENCE: 5
ccgggccgcc tcgctcgctc ccagctctgt cagtggcccg cggggcccga tcgctgcgcc      60
cgcggccagg gccgaggcag gcctgacccg gggccgggca gcccgcgcga ctttcggaac     120
atggcaaccc gtgtgtgtct catcccagaa agagaagact ttaaccactg tgatgcctga     180
gaatccagtg tgacgtttct ccagatactt catgctgttc acctgtgtcc tcgccgcacc     240
actgccgcac acgactcctg aacc atg ggg gaa aac gag gat gag aag cag        291
                         Met Gly Glu Asn Glu Asp Glu Lys Gln
                           1               5 gcc cag gcg ggg cag gtt ttt gag aac ttt gtc cag gca tcc acg tgc       339
Ala Gln Ala Gly Gln Val Phe Glu Asn Phe Val Gln Ala Ser Thr Cys
 10              15                  20                  25 aaa ggt acc ctc cag gcc ttc aac att ctc aca cga cac ctg gac cta       387
Lys Gly Thr Leu Gln Ala Phe Asn Ile Leu Thr Arg His Leu Asp Leu
                 30                  35                  40 gac cct ctg gac cac aga aac ttt tat tcc aag ctc aag tcc aag gtg       435
Asp Pro Leu Asp His Arg Asn Phe Tyr Ser Lys Leu Lys Ser Lys Val
             45                  50                  55 acc acc tgg aaa gcc aaa gcc ctg tgg tac aaa ttg gat aag cgt ggt       483
Thr Thr Trp Lys Ala Lys Ala Leu Trp Tyr Lys Leu Asp Lys Arg Gly
         60                  65                  70 tcc cac aaa gag tat aag cga ggg aag tcg tgc acg aac acc aag tgt       531
Ser His Lys Glu Tyr Lys Arg Gly Lys Ser Cys Thr Asn Thr Lys Cys
     75                  80                  85 ctc ata gtt ggg gga gga ccc tgt ggc ttg cgc act gcc att gaa ctt       579
Leu Ile Val Gly Gly Gly Pro Cys Gly Leu Arg Thr Ala Ile Glu Leu
 90                  95                 100                 105 gcc tac ctg gga gcc aaa gtg gtc gtg gtg gag aag agg gac tcc ttc       627
Ala Tyr Leu Gly Ala Lys Val Val Val Val Glu Lys Arg Asp Ser Phe
                110                 115                 120 tcc cgg aac aac gtg cta cac ctc tgg cct ttc acc atc cat gac ctt       675
Ser Arg Asn Asn Val Leu His Leu Trp Pro Phe Thr Ile His Asp Leu
            125                 130                 135 cgg ggc ctg gga gcc aag aag ttc tat ggg aag ttc tgt gct ggc tcc       723
Arg Gly Leu Gly Ala Lys Lys Phe Tyr Gly Lys Phe Cys Ala Gly Ser
        140                 145                 150 atc gac cat atc agt att cgc caa cta cag ctc atc cta ttc aag gtg       771
Ile Asp His Ile Ser Ile Arg Gln Leu Gln Leu Ile Leu Phe Lys Val
    155                 160                 165
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | ctg | atg | ctg | gga | gtt | gaa | atc | cat | gtg | aat | gtg | gag | ttc | gtg | aag | 819  |
| Ala | Leu | Met | Leu | Gly | Val | Glu | Ile | His | Val | Asn | Val | Glu | Phe | Val | Lys |      |
| 170 |     |     |     |     | 175 |     |     |     |     | 180 |     |     |     |     | 185 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtt | cta | gag | cct | cct | gaa | gat | caa | gaa | aat | caa | aaa | att | ggc | tgg | cgg | 867  |
| Val | Leu | Glu | Pro | Pro | Glu | Asp | Gln | Glu | Asn | Gln | Lys | Ile | Gly | Trp | Arg |      |
|     |     |     |     | 190 |     |     |     |     | 195 |     |     |     |     | 200 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gca | gaa | ttt | ctc | cct | aca | gac | cat | tct | ctg | tcg | gag | ttt | gag | ttt | gac | 915  |
| Ala | Glu | Phe | Leu | Pro | Thr | Asp | His | Ser | Leu | Ser | Glu | Phe | Glu | Phe | Asp |      |
|     |     |     |     | 205 |     |     |     |     | 210 |     |     |     |     | 215 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtc | atc | att | ggt | gcc | gat | ggc | cgc | agg | aac | acc | ctg | gaa | ggg | ttc | aga | 963  |
| Val | Ile | Ile | Gly | Ala | Asp | Gly | Arg | Arg | Asn | Thr | Leu | Glu | Gly | Phe | Arg |      |
|     |     || 220 |     |     |     |     | 225 |     |     |     |     | 230 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aga | aaa | gaa | ttc | cgt | ggg | aag | ctg | gcg | att | gcc | atc | acc | gcc | aac | ttc | 1011 |
| Arg | Lys | Glu | Phe | Arg | Gly | Lys | Leu | Ala | Ile | Ala | Ile | Thr | Ala | Asn | Phe |      |
|     | 235 |     |     |     |     | 240 |     |     |     |     | 245 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ata | aac | aga | aac | agc | aca | gcg | gaa | gcc | aag | gtg | gaa | gag | att | agt | ggt | 1059 |
| Ile | Asn | Arg | Asn | Ser | Thr | Ala | Glu | Ala | Lys | Val | Glu | Glu | Ile | Ser | Gly |      |
| 250 |     |     |     |     | 255 |     |     |     |     | 260 |     |     |     |     | 265 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | gct | ttc | atc | ttc | aat | cag | aaa | ttt | ttt | cag | gac | ctt | aaa | gaa | gaa | 1107 |
| Val | Ala | Phe | Ile | Phe | Asn | Gln | Lys | Phe | Phe | Gln | Asp | Leu | Lys | Glu | Glu |      |
|     |     |     |     | 270 |     |     |     |     | 275 |     |     |     |     | 280 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aca | ggc | ata | gat | ctt | gag | aac | att | gtt | tac | tac | aag | gac | tgc | acc | cac | 1155 |
| Thr | Gly | Ile | Asp | Leu | Glu | Asn | Ile | Val | Tyr | Tyr | Lys | Asp | Cys | Thr | His |      |
|     |     |     |     | 285 |     |     |     |     | 290 |     |     |     |     | 295 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tat | ttt | gta | atg | aca | gcc | aag | aag | cag | agc | ctg | ctc | gac | aaa | ggt | gtc | 1203 |
| Tyr | Phe | Val | Met | Thr | Ala | Lys | Lys | Gln | Ser | Leu | Leu | Asp | Lys | Gly | Val |      |
|     |     |     | 300 |     |     |     |     | 305 |     |     |     |     | 310 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | att | aac | gac | tac | atc | gac | aca | gag | atg | ctg | ctg | tgt | gcg | gag | aac | 1251 |
| Ile | Ile | Asn | Asp | Tyr | Ile | Asp | Thr | Glu | Met | Leu | Leu | Cys | Ala | Glu | Asn |      |
|     | 315 |     |     |     |     | 320 |     |     |     |     | 325 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | aac | caa | gac | aac | ctg | cta | tcc | tat | gcc | cgg | gaa | gct | gca | gac | ttt | 1299 |
| Val | Asn | Gln | Asp | Asn | Leu | Leu | Ser | Tyr | Ala | Arg | Glu | Ala | Ala | Asp | Phe |      |
| 330 |     |     |     |     | 335 |     |     |     |     | 340 |     |     |     |     | 345 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | acc | aac | tac | cag | ctg | cca | tcc | tta | gac | ttt | gcc | atg | aac | cac | tat | 1347 |
| Ala | Thr | Asn | Tyr | Gln | Leu | Pro | Ser | Leu | Asp | Phe | Ala | Met | Asn | His | Tyr |      |
|     |     |     |     | 350 |     |     |     |     | 355 |     |     |     |     | 360 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggg | cag | cct | gat | gtg | gcc | atg | ttt | gac | ttt | acc | tgc | atg | tat | gcc | tca | 1395 |
| Gly | Gln | Pro | Asp | Val | Ala | Met | Phe | Asp | Phe | Thr | Cys | Met | Tyr | Ala | Ser |      |
|     |     |     | 365 |     |     |     |     | 370 |     |     |     |     | 375 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gag | aac | gcg | gcc | ctg | gtg | cgg | gag | cgg | cag | gcg | cac | cag | ctg | ctc | gtg | 1443 |
| Glu | Asn | Ala | Ala | Leu | Val | Arg | Glu | Arg | Gln | Ala | His | Gln | Leu | Leu | Val |      |
|     |     | 380 |     |     |     |     | 385 |     |     |     |     | 390 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | ctt | gtg | ggt | gac | agc | ttg | ctt | gag | cca | ttt | tgg | ccc | atg | ggt | aca | 1491 |
| Ala | Leu | Val | Gly | Asp | Ser | Leu | Leu | Glu | Pro | Phe | Trp | Pro | Met | Gly | Thr |      |
| 395 |     |     |     |     | 400 |     |     |     |     | 405 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | tgt | gcc | cgt | ggc | ttc | ctg | gca | gcc | ttt | gac | acg | gca | tgg | atg | gtg | 1539 |
| Gly | Cys | Ala | Arg | Gly | Phe | Leu | Ala | Ala | Phe | Asp | Thr | Ala | Trp | Met | Val |      |
| 410 |     |     |     |     | 415 |     |     |     |     | 420 |     |     |     |     | 425 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aag | agc | tgg | aac | cag | ggc | acc | cct | ccc | ctg | gag | ctg | ctg | gct | gaa | agg | 1587 |
| Lys | Ser | Trp | Asn | Gln | Gly | Thr | Pro | Pro | Leu | Glu | Leu | Leu | Ala | Glu | Arg |      |
|     |     |     | 430 |     |     |     |     | 435 |     |     |     |     | 440 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaa | agt | ctc | tac | cgg | ctg | tta | cct | cag | aca | acc | ccg | gag | aac | atc | aac | 1635 |
| Glu | Ser | Leu | Tyr | Arg | Leu | Leu | Pro | Gln | Thr | Thr | Pro | Glu | Asn | Ile | Asn |      |
|     |     |     | 445 |     |     |     |     | 450 |     |     |     |     | 455 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aag | aac | ttt | gag | cag | tac | acg | ttg | gac | cca | ggg | aca | cgg | tac | cca | aac | 1683 |
| Lys | Asn | Phe | Glu | Gln | Tyr | Thr | Leu | Asp | Pro | Gly | Thr | Arg | Tyr | Pro | Asn |      |
|     |     |     | 460 |     |     |     |     | 465 |     |     |     |     | 470 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctc | aac | tca | cac | tgt | gtc | agg | ccc | cat | cag | gtg | aag | cat | ttg | tat | atc | 1731 |
| Leu | Asn | Ser | His | Cys | Val | Arg | Pro | His | Gln | Val | Lys | His | Leu | Tyr | Ile |      |
|     |     |     | 475 |     |     |     |     | 480 |     |     |     |     | 485 |     |     |      |

```
act aag gag ctg gag cac tac cct ctc gag aga ctg ggc tcg gtg agg          1779
Thr Lys Glu Leu Glu His Tyr Pro Leu Glu Arg Leu Gly Ser Val Arg
490                 495                 500                 505 aga tct gtc aac ctc tcc agg aag gag tca gat atc cgg ccc agc aag          1827
Arg Ser Val Asn Leu Ser Arg Lys Glu Ser Asp Ile Arg Pro Ser Lys
                510                 515                 520 ctc ctg acc tgg tgc cag cag cag aca gag ggc tac cag cat gtc aac          1875
Leu Leu Thr Trp Cys Gln Gln Gln Thr Glu Gly Tyr Gln His Val Asn
            525                 530                 535 gtc acc gac ctg acc aca tcc tgg cgc agt ggg ttg gcc ctg tgt gcc          1923
Val Thr Asp Leu Thr Thr Ser Trp Arg Ser Gly Leu Ala Leu Cys Ala
        540                 545                 550 atc atc cac cgc ttc cgg cct gag ctc atc aac ttt gac tct ttg aat          1971
Ile Ile His Arg Phe Arg Pro Glu Leu Ile Asn Phe Asp Ser Leu Asn
    555                 560                 565 gaa gat gat gct gtg gag aac aac cag ctc gca ttt gat gtg gcc gag          2019
Glu Asp Asp Ala Val Glu Asn Asn Gln Leu Ala Phe Asp Val Ala Glu
570                 575                 580                 585 cga gag ttt ggg atc cct cca gtg acc acg ggc aaa gag atg gca tct          2067
Arg Glu Phe Gly Ile Pro Pro Val Thr Thr Gly Lys Glu Met Ala Ser
                590                 595                 600 gcc cag gag cct gac aag ctc agc atg gtc atg tac ctc tcc aag ttc          2115
Ala Gln Glu Pro Asp Lys Leu Ser Met Val Met Tyr Leu Ser Lys Phe
            605                 610                 615 tac gag ctc ttc cgg ggc acc cca ctg agg ccc gtg gat tct tgg cgc          2163
Tyr Glu Leu Phe Arg Gly Thr Pro Leu Arg Pro Val Asp Ser Trp Arg
        620                 625                 630 aaa aac tat gga gaa aat gct gac ctc agc ttg gcc aaa tca tcc att          2211
Lys Asn Tyr Gly Glu Asn Ala Asp Leu Ser Leu Ala Lys Ser Ser Ile
    635                 640                 645 tct aat aac tat ctc aac ctc aca ttt cca agg aag agg act cca cgg          2259
Ser Asn Asn Tyr Leu Asn Leu Thr Phe Pro Arg Lys Arg Thr Pro Arg
650                 655                 660                 665 gtg gat ggt caa acc gga gag aat gac atg aac aaa cgg aga cgg aag          2307
Val Asp Gly Gln Thr Gly Glu Asn Asp Met Asn Lys Arg Arg Arg Lys
                670                 675                 680 ggc ttc acc aac ctg gac gag cct tca aac ttt tcc agc cgt agc ttg          2355
Gly Phe Thr Asn Leu Asp Glu Pro Ser Asn Phe Ser Ser Arg Ser Leu
            685                 690                 695 ggc tcc aat caa gag tgt ggg agc agt aag gaa ggt gga aat cag aac          2403
Gly Ser Asn Gln Glu Cys Gly Ser Ser Lys Glu Gly Gly Asn Gln Asn
        700                 705                 710 aaa gtc aag tcc atg gcg aat cag ctg ctg gcc aag ttt gag gag agc          2451
Lys Val Lys Ser Met Ala Asn Gln Leu Leu Ala Lys Phe Glu Glu Ser
    715                 720                 725 act cgg aac ccc tca ctc atg aag cag gaa tct atg cga aag tca ttt          2499
Thr Arg Asn Pro Ser Leu Met Lys Gln Glu Ser Met Arg Lys Ser Phe
730                 735                 740                 745 ccc ctt aac ctg gga ggc agc gac acg tgt tac ttc tgt aag aaa cgt          2547
Pro Leu Asn Leu Gly Gly Ser Asp Thr Cys Tyr Phe Cys Lys Lys Arg
                750                 755                 760 gtg tac gtg atg gaa cgg ctg agc gcc gag ggc cac ttc ttc cac cgg          2595
Val Tyr Val Met Glu Arg Leu Ser Ala Glu Gly His Phe Phe His Arg
            765                 770                 775 gag tgt ttc cgc tgc agc atc tgt gcc acc acc ttg cgc ctg gcc gcc          2643
Glu Cys Phe Arg Cys Ser Ile Cys Ala Thr Thr Leu Arg Leu Ala Ala
        780                 785                 790 tac acc ttt gac tgc gat gaa ggc aaa ttt tac tgc aag cct cac ttc          2691
Tyr Thr Phe Asp Cys Asp Glu Gly Lys Phe Tyr Cys Lys Pro His Phe
```

-continued

```
                  795                 800                 805
att cac tgt aaa acc aat agc aaa caa cgg aag aga cgg gca gag ttg      2739
Ile His Cys Lys Thr Asn Ser Lys Gln Arg Lys Arg Arg Ala Glu Leu
810             815                 820                 825 aag caa caa aga gag gag gag gca aca tgg caa gag cag gaa gcc cct      2787
Lys Gln Gln Arg Glu Glu Glu Ala Thr Trp Gln Glu Gln Glu Ala Pro
                830                 835                 840 cgg aga gac act ccc acc gaa agt tct tgc gca gtg gcc gcc att ggc      2835
Arg Arg Asp Thr Pro Thr Glu Ser Ser Cys Ala Val Ala Ala Ile Gly
            845                 850                 855 acc ctg gaa ggc agc ccc cca ggt atc tcc acc tcc ttc ttt agg aag      2883
Thr Leu Glu Gly Ser Pro Pro Gly Ile Ser Thr Ser Phe Phe Arg Lys
        860                 865                 870 gtg ctg ggc tgg ccc ctc agg ctg ccg agg gac ctg tgt aac tgg atg      2931
Val Leu Gly Trp Pro Leu Arg Leu Pro Arg Asp Leu Cys Asn Trp Met
    875                 880                 885 cag gga ctc ctg caa gct gct ggc ctc cat atc agg gac aat gct tac      2979
Gln Gly Leu Leu Gln Ala Ala Gly Leu His Ile Arg Asp Asn Ala Tyr
890                 895                 900                 905 aac tac tgc tac atg tac gag ctc ctg agc ctg ggg ctg cca ctc ctc      3027
Asn Tyr Cys Tyr Met Tyr Glu Leu Leu Ser Leu Gly Leu Pro Leu Leu
                910                 915                 920 tgg gcg ttc tct gag gtc ctg gca gcc atg tac agg gaa tct gag ggc      3075
Trp Ala Phe Ser Glu Val Leu Ala Ala Met Tyr Arg Glu Ser Glu Gly
                925                 930                 935 tcc ctc gag agc atc tgc aac tgg gtg ctc agg tgc ttc cca gtc aag      3123
Ser Leu Glu Ser Ile Cys Asn Trp Val Leu Arg Cys Phe Pro Val Lys
            940                 945                 950 ctc cgc tga catggctggc tgccccaaag tgccttcaca tttccaggga              3172
Leu Arg
    955 ggcttcagat ggcagtgcgt ttgcagtttg ctcaggctct ggccaggaag cctagcattc    3232 tctaagcaat tagctcaaag ccaaagaatt tcacatgggc acctccgcc tggccttatc     3292 agggtgaaca tctactcacg gtgctagggc cagggatgat atgaaggatc ttttctatag    3352 cttttgtgagc catacttctg ggtttacatt tcaatttttt taattttaat tagcccagag   3412 aaagcatttt tttctatgag tgtcaatttt tctaaacatg ggtttgaagc ttataaccag    3472 ttttataaac cccttgaaca ctgcagtgag ttatcaaagc cactgcctgc aaagtggatg    3532 atttaagatt ttacacgcat gaaaatgagt gtgccatctc ctgaccagtg cctttgact     3592 taggtaccca gatgccactt gtcagcagca ggatactttt tacaacacga aagcataatt    3652 attttagaag aagagagtag aagggcagaa tagaattcaa cttacagaag cacggagcag    3712 tgtgtggttg gctgttatct gtcccctgg gaggaggact gttttgctcc cttgttttga     3772 tgttaaacag tagcttaaag gctttccccc ccataccaac tcacagccaa atgacaaaga    3832 accgtggggt ttcaacagat tctacaaaca tgcattttcc cttccactca atgggcactg    3892 cagggaaagc ccattggcat ttgaccatgg agctgatgca gtgccaaaga tgagctcttt    3952 caactgatgg cattttagcc cctgtggctc ccagcggatc cccagcccg ggctgcaggc     4012 tgagccaagg ctgtgcaggg tccatattgg tcaggccaag tggagtggaa gactctgtcc    4072 acttatgtgg tgtcctttgg gactgagggg gtttgttagc acatcaggct attgctggga    4132 agcgtggcct gcccagtgag cattgcctgt ggacatcctg actgcttagc tgctccgctg    4192 ccacacatat gtggtcaaaa cagaaaccaa tttcacactg ccctgggaaa ggaatgggtc    4252 tgacctccag gggaagctct accatatctt gactggcagg gaaggctggg agtggaagct    4312
```

```
atttatggac tgatccaaag gacatatgca tgagtaaggg taaaaatgag catgcaggtc    4372
cacctgtgtt cttactctgg gtatctagaa gagtcctcag ctctccctac tccacgctgc    4432
ctagacatac acagctgcag ggtctggctg aacaatcaag gggccgccag agaaaggcca    4492
tctacggtgc gcagtgtatc tggagttgct gggcccaaga tagctctgtg gagttatcac    4552
tagagatgcc tctggattaa ctaagaggtg tgcctgggtg tgggtgagga gtcagaacct    4612
ttgagagctt tgagatgaca gtttctatgg ggcgggaaga aggaggtgca tttctacaaa    4672
cacttccctg aaatccttgg gaaaaacaga ggcatggccg tggccaactc tgtgggaact    4732
ggcgcctctg tccttgttgg cactgttctc agtccgatga cttgcattgt gttttctcca    4792
attttttgctg ggattttaat gttcagcatg gtgggaggaa ccctttgattc cttttgtttg   4852
agtatagaaa gtaaattttt gaggtcatga tgtgaacggc catgttattg tgattatctt    4912
cagctcagga taggctgaga tgctttgtgg agtgttccat gaagcccgag tcggaatctc    4972
tgactgtcgt gtacagccat aaggagactg gtttgaatta ctgtggcgag acagggcgtg    5032
cctgtcagaa atctgagatg tttgtacgct ctgagatgtt gaacctttct ggtgggcagc    5092
accgacaccc agggtggac ccccgaggat gaatgcctct aggcctccgc aacatattca     5152
agaatgaatg ggagacgcta gagtaaaatg ggggcagaga ggatatcagg gagcaagatg    5212
caaactgtgt gcatccactc tcgtaaacaa gtagctggtc acaaccagaa aggttcatct    5272
ctcctaagca aacagcgact cttttcagagg aagtttccct cttttcaatcg tggccttatt   5332
ttcaactccg gtgccttctc gtgatgttaa tcatttcctt ttttcccac actaagctct     5392
ctttttctatc tttctctctc tttccaatct tacgccatgg ccatcagttc atttcagcct   5452
tccagtgcta cacccacttc ttggctgaca cacttctgct ctaaggtgac tggttttctt    5512
gccaatttc aaagagtggt actaacccc aaccgctttt ccgcaccccg tcctctccgc      5572
cagcagtact ggttgcacta actgtgagtg tcttgcatac tgatggactc atttggtggc    5632
atggttggct aacagcatgg cggggggtgt tcagcttgag acccatgcct gtgttcattt    5692
cccatggagc tggcagcctg gtctacccca agtgcatgcc ccgcctctcc tctctccctt    5752
gggtctgcct gcgtgcatgc ttctccagtt gcgtctgcga agctacctac tttcttggga    5812
gggtcgacct tgatcatgaa acaataccat gagggggcct ctgtcacctt tgaaaagaac    5872
acttttgag cagcctcaaa aagctcatac ataccagcgc cttcttaaat tggctctaat     5932
gtaaagattg ttaatgtcat ttatcaaaac cataggtgat tatttggagg gatttaaaaa    5992
acttaattac tctcaggcct catcccaagc ttgacacatg ctctgtaggt tgaacacata    6052
atcacaaata ttctagcaaa tgctgccttg gttcagcct gcactgtaga cccaagggtt     6112
ttgctgtggc tcttcttatc tcccttggct cataaagccc cagatgatgc cagagcttca    6172
attagagcca tcatcatccc aggcagggat atctttgaga aatgactcag ttcagcccca    6232
ggccctgtg actctgctta aagcacacat ttctgctgac tcttgtacct ggggcagcag     6292
gataatcacc aacacactct taacgagaaa caacacacca agcaccgtgg agctgtccta    6352
ggcaacactc gcggtctcag gctgcggtgg gcgtctgtcc tgcatgtggc ccagaccacc    6412
ctgaccccg ggcctgcctg cctggccctg catgctgcac gctcactgta tttgtgcaga     6472
tcctggccag tacaaagtcg ttgctcttgt cttatcttct cttacagagt ctccctccct    6532
ttatagaatg tcaaccaaag agtgccctcc tcccctctca gcctcctctt tagctagcct    6592
ccccatctca tcacaacgca tgtctgtgac ctttggtaat catttacagt gccacacgga    6652
```

```
accctgtatt ttgcacacag caaaacaaac aatgtttagc tttatttatg gtatttgatg    6712
ctgtaaatgg aaataaatat tgttctttat                                     6742
```

<210> SEQ ID NO 6
<211> LENGTH: 955
<212> TYPE: PRT
<213> ORGANISM: Homo sapiens

<400> SEQUENCE: 6

```
Met Gly Glu Asn Glu Asp Glu Lys Gln Ala Gln Ala Gly Gln Val Phe
1               5                   10                  15

Glu Asn Phe Val Gln Ala Ser Thr Cys Lys Gly Thr Leu Gln Ala Phe
            20                  25                  30

Asn Ile Leu Thr Arg His Leu Asp Leu Asp Pro Leu Asp His Arg Asn
        35                  40                  45

Phe Tyr Ser Lys Leu Lys Ser Lys Val Thr Thr Trp Lys Ala Lys Ala
    50                  55                  60

Leu Trp Tyr Lys Leu Asp Lys Arg Gly Ser His Lys Glu Tyr Lys Arg
65                  70                  75                  80

Gly Lys Ser Cys Thr Asn Thr Lys Cys Leu Ile Val Gly Gly Gly Pro
                85                  90                  95

Cys Gly Leu Arg Thr Ala Ile Glu Leu Ala Tyr Leu Gly Ala Lys Val
            100                 105                 110

Val Val Val Glu Lys Arg Asp Ser Phe Ser Arg Asn Asn Val Leu His
        115                 120                 125

Leu Trp Pro Phe Thr Ile His Asp Leu Arg Gly Leu Gly Ala Lys Lys
    130                 135                 140

Phe Tyr Gly Lys Phe Cys Ala Gly Ser Ile Asp His Ile Ser Ile Arg
145                 150                 155                 160

Gln Leu Gln Leu Ile Leu Phe Lys Val Ala Leu Met Leu Gly Val Glu
                165                 170                 175

Ile His Val Asn Val Glu Phe Val Lys Val Leu Glu Pro Pro Glu Asp
            180                 185                 190

Gln Glu Asn Gln Lys Ile Gly Trp Arg Ala Glu Phe Leu Pro Thr Asp
        195                 200                 205

His Ser Leu Ser Glu Phe Glu Phe Asp Val Ile Gly Ala Asp Gly
    210                 215                 220

Arg Arg Asn Thr Leu Glu Gly Phe Arg Arg Lys Glu Phe Arg Gly Lys
225                 230                 235                 240

Leu Ala Ile Ala Ile Thr Ala Asn Phe Ile Asn Arg Asn Ser Thr Ala
                245                 250                 255

Glu Ala Lys Val Glu Glu Ile Ser Gly Val Ala Phe Ile Phe Asn Gln
            260                 265                 270

Lys Phe Phe Gln Asp Leu Lys Glu Glu Thr Gly Ile Asp Leu Glu Asn
        275                 280                 285

Ile Val Tyr Tyr Lys Asp Cys Thr His Tyr Phe Val Met Thr Ala Lys
    290                 295                 300

Lys Gln Ser Leu Leu Asp Lys Gly Val Ile Ile Asn Asp Tyr Ile Asp
305                 310                 315                 320

Thr Glu Met Leu Leu Cys Ala Glu Asn Val Asn Gln Asp Asn Leu Leu
                325                 330                 335

Ser Tyr Ala Arg Glu Ala Ala Asp Phe Ala Thr Asn Tyr Gln Leu Pro
            340                 345                 350

Ser Leu Asp Phe Ala Met Asn His Tyr Gly Gln Pro Asp Val Ala Met
```

-continued

```
            355                 360                 365
Phe Asp Phe Thr Cys Met Tyr Ala Ser Glu Asn Ala Ala Leu Val Arg
    370                 375                 380
Glu Arg Gln Ala His Gln Leu Leu Val Ala Leu Val Gly Asp Ser Leu
385                 390                 395                 400
Leu Glu Pro Phe Trp Pro Met Gly Thr Gly Cys Ala Arg Gly Phe Leu
                405                 410                 415
Ala Ala Phe Asp Thr Ala Trp Met Val Lys Ser Trp Asn Gln Gly Thr
                420                 425                 430
Pro Pro Leu Glu Leu Leu Ala Glu Arg Glu Ser Leu Tyr Arg Leu Leu
            435                 440                 445
Pro Gln Thr Thr Pro Glu Asn Ile Asn Lys Asn Phe Glu Gln Tyr Thr
    450                 455                 460
Leu Asp Pro Gly Thr Arg Tyr Pro Asn Leu Asn Ser His Cys Val Arg
465                 470                 475                 480
Pro His Gln Val Lys His Leu Tyr Ile Thr Lys Glu Leu Glu His Tyr
                485                 490                 495
Pro Leu Glu Arg Leu Gly Ser Val Arg Arg Ser Val Asn Leu Ser Arg
            500                 505                 510
Lys Glu Ser Asp Ile Arg Pro Ser Lys Leu Leu Thr Trp Cys Gln Gln
    515                 520                 525
Gln Thr Glu Gly Tyr Gln His Val Asn Val Thr Asp Leu Thr Thr Ser
    530                 535                 540
Trp Arg Ser Gly Leu Ala Leu Cys Ala Ile Ile His Arg Phe Arg Pro
545                 550                 555                 560
Glu Leu Ile Asn Phe Asp Ser Leu Asn Glu Asp Asp Ala Val Glu Asn
                565                 570                 575
Asn Gln Leu Ala Phe Asp Val Ala Glu Arg Glu Phe Gly Ile Pro Pro
                580                 585                 590
Val Thr Thr Gly Lys Glu Met Ala Ser Ala Gln Glu Pro Asp Lys Leu
            595                 600                 605
Ser Met Val Met Tyr Leu Ser Lys Phe Tyr Glu Leu Phe Arg Gly Thr
    610                 615                 620
Pro Leu Arg Pro Val Asp Ser Trp Arg Lys Asn Tyr Gly Glu Asn Ala
625                 630                 635                 640
Asp Leu Ser Leu Ala Lys Ser Ser Ile Ser Asn Asn Tyr Leu Asn Leu
                645                 650                 655
Thr Phe Pro Arg Lys Arg Thr Pro Arg Val Asp Gly Gln Thr Gly Glu
                660                 665                 670
Asn Asp Met Asn Lys Arg Arg Lys Gly Phe Thr Asn Leu Asp Glu
            675                 680                 685
Pro Ser Asn Phe Ser Ser Arg Ser Leu Gly Ser Asn Gln Glu Cys Gly
    690                 695                 700
Ser Ser Lys Glu Gly Gly Asn Gln Asn Lys Val Lys Ser Met Ala Asn
705                 710                 715                 720
Gln Leu Leu Ala Lys Phe Glu Glu Ser Thr Arg Asn Pro Ser Leu Met
                725                 730                 735
Lys Gln Glu Ser Met Arg Lys Ser Phe Pro Leu Asn Leu Gly Gly Ser
                740                 745                 750
Asp Thr Cys Tyr Phe Cys Lys Lys Arg Val Tyr Val Met Glu Arg Leu
            755                 760                 765
Ser Ala Glu Gly His Phe Phe His Arg Glu Cys Phe Arg Cys Ser Ile
    770                 775                 780
```

-continued

```
Cys Ala Thr Thr Leu Arg Leu Ala Ala Tyr Thr Phe Asp Cys Asp Glu
785                 790                 795                 800

Gly Lys Phe Tyr Cys Lys Pro His Phe Ile His Cys Lys Thr Asn Ser
            805                 810                 815

Lys Gln Arg Lys Arg Ala Glu Leu Lys Gln Gln Arg Glu Glu Glu
        820                 825                 830

Ala Thr Trp Gln Glu Gln Glu Ala Pro Arg Arg Asp Thr Pro Thr Glu
        835                 840                 845

Ser Ser Cys Ala Val Ala Ala Ile Gly Thr Leu Glu Gly Ser Pro Pro
850                 855                 860

Gly Ile Ser Thr Ser Phe Phe Arg Lys Val Leu Gly Trp Pro Leu Arg
865                 870                 875                 880

Leu Pro Arg Asp Leu Cys Asn Trp Met Gln Gly Leu Leu Gln Ala Ala
                885                 890                 895

Gly Leu His Ile Arg Asp Asn Ala Tyr Asn Tyr Cys Tyr Met Tyr Glu
            900                 905                 910

Leu Leu Ser Leu Gly Leu Pro Leu Leu Trp Ala Phe Ser Glu Val Leu
        915                 920                 925

Ala Ala Met Tyr Arg Glu Ser Glu Gly Ser Leu Glu Ser Ile Cys Asn
930                 935                 940

Trp Val Leu Arg Cys Phe Pro Val Lys Leu Arg
945                 950                 955

<210> SEQ ID NO 7
<211> LENGTH: 20
<212> TYPE: DNA
<213> ORGANISM: Artificial
<220> FEATURE:
<223> OTHER INFORMATION: Artifitially synthesized primer sequence for
      RT-PCR

<400> SEQUENCE: 7
ccgacactct gggtaggaga                                              20

<210> SEQ ID NO 8
<211> LENGTH: 20
<212> TYPE: DNA
<213> ORGANISM: Artificial
<220> FEATURE:
<223> OTHER INFORMATION: Artifitially synthesized primer sequence for
      RT-PCR

<400> SEQUENCE: 8
tacgtgagct ctgaggacca                                              20

<210> SEQ ID NO 9
<211> LENGTH: 23
<212> TYPE: DNA
<213> ORGANISM: Artificial
<220> FEATURE:
<223> OTHER INFORMATION: Artifitially synthesized primer sequence for
      RT-PCR

<400> SEQUENCE: 9
tgaagcaaca aagagaggag gag                                          23

<210> SEQ ID NO 10
<211> LENGTH: 23
<212> TYPE: DNA
<213> ORGANISM: Artificial
<220> FEATURE:
```

```
<223> OTHER INFORMATION: Artifitially synthesized primer sequence for
      RT-PCR

<400> SEQUENCE: 10
ccgtgtggca ctgtaaatga tta                                              23

<210> SEQ ID NO 11
<211> LENGTH: 23
<212> TYPE: DNA
<213> ORGANISM: Artificial
<220> FEATURE:
<223> OTHER INFORMATION: Artifitially synthesized primer sequence for
      RT-PCR

<400> SEQUENCE: 11
catccacgaa actaccttca act                                              23

<210> SEQ ID NO 12
<211> LENGTH: 23
<212> TYPE: DNA
<213> ORGANISM: Artificial
<220> FEATURE:
<223> OTHER INFORMATION: Artifitially synthesized primer sequence for
      RT-PCR

<400> SEQUENCE: 12
tctccttaga gagaagtggg gtg                                              23

<210> SEQ ID NO 13
<211> LENGTH: 20
<212> TYPE: DNA
<213> ORGANISM: Artificial
<220> FEATURE:
<223> OTHER INFORMATION: Artifitially synthesized primer sequence for
      RT-PCR

<400> SEQUENCE: 13
ccgacactct gggtaggaga                                                  20

<210> SEQ ID NO 14
<211> LENGTH: 20
<212> TYPE: DNA
<213> ORGANISM: Artificial
<220> FEATURE:
<223> OTHER INFORMATION: Artifitially synthesized primer sequence for
      RT-PCR

<400> SEQUENCE: 14
tacgtgagct ctgaggacca                                                  20

<210> SEQ ID NO 15
<211> LENGTH: 20
<212> TYPE: DNA
<213> ORGANISM: Artificial
<220> FEATURE:
<223> OTHER INFORMATION: Artifitially synthesized primer sequence for
      RT-PCR

<400> SEQUENCE: 15
gcagggatat ctttgagaaa                                                  20

<210> SEQ ID NO 16
<211> LENGTH: 20
<212> TYPE: DNA
<213> ORGANISM: Artificial
<220> FEATURE:
<223> OTHER INFORMATION: Artifitially synthesized primer sequence for
```

```
                                          -continued
          RT-PCR

<400> SEQUENCE: 16
ccaggatctg cacaaataca                                                   20

<210> SEQ ID NO 17
<211> LENGTH: 50
<212> TYPE: DNA
<213> ORGANISM: Artificial
<220> FEATURE:
<223> OTHER INFORMATION: Artifitially synthesized primer sequence for
      RT-PCR

<400> SEQUENCE: 17
cgtggatccc agaccgtgca tcatgggcac atctgaagaa ggaaacttgc                  50

<210> SEQ ID NO 18
<211> LENGTH: 32
<212> TYPE: DNA
<213> ORGANISM: Artificial
<220> FEATURE:
<223> OTHER INFORMATION: Artifitially synthesized primer sequence for
      RT-PCR

<400> SEQUENCE: 18
aatctcgagt caggggcaga aggggaataa gg                                     32

<210> SEQ ID NO 19
<211> LENGTH: 29
<212> TYPE: DNA
<213> ORGANISM: Artificial
<220> FEATURE:
<223> OTHER INFORMATION: Artifitially synthesized primer sequence for
      RT-PCR

<400> SEQUENCE: 19
cccaagctta tgggggaaaa cgaggatga                                         29

<210> SEQ ID NO 20
<211> LENGTH: 38
<212> TYPE: DNA
<213> ORGANISM: Artificial
<220> FEATURE:
<223> OTHER INFORMATION: Artifitially synthesized primer sequence for
      RT-PCR

<400> SEQUENCE: 20
ttttcctttt gcggccgcgc ggagcttgac tgggaagc                               38

<210> SEQ ID NO 21
<211> LENGTH: 19
<212> TYPE: DNA
<213> ORGANISM: Artificial
<220> FEATURE:
<223> OTHER INFORMATION: Artifitially synthesized target sequence for
      SiRNA

<400> SEQUENCE: 21
tagggcccat ggggcccgg                                                    19

<210> SEQ ID NO 22
<211> LENGTH: 19
<212> TYPE: DNA
<213> ORGANISM: Artificial
<220> FEATURE:
<223> OTHER INFORMATION: Artifitially synthesized target sequence for
      SiRNA
```

-continued

```
<400> SEQUENCE: 22
accagttggg cccaaaggc                                                19

<210> SEQ ID NO 23
<211> LENGTH: 19
<212> TYPE: DNA
<213> ORGANISM: Artificial
<220> FEATURE:
<223> OTHER INFORMATION: Artifitially synthesized target sequence for
      SiRNA

<400> SEQUENCE: 23
aggcccaatg ttgcccctt                                                19

<210> SEQ ID NO 24
<211> LENGTH: 19
<212> TYPE: DNA
<213> ORGANISM: Artificial
<220> FEATURE:
<223> OTHER INFORMATION: Artifitially synthesized target sequence for
      SiRNA

<400> SEQUENCE: 24
tgttgcccct tggccctc                                                 19

<210> SEQ ID NO 25
<211> LENGTH: 19
<212> TYPE: DNA
<213> ORGANISM: Artificial
<220> FEATURE:
<223> OTHER INFORMATION: Artifitially synthesized target sequence for
      SiRNA

<400> SEQUENCE: 25
gaagcagcac gacttcttc                                                19

<210> SEQ ID NO 26
<211> LENGTH: 19
<212> TYPE: DNA
<213> ORGANISM: Artificial
<220> FEATURE:
<223> OTHER INFORMATION: Artifitially synthesized target sequence for
      SiRNA

<400> SEQUENCE: 26
gctgctggcc tccatatca                                                19

<210> SEQ ID NO 27
<211> LENGTH: 19
<212> TYPE: DNA
<213> ORGANISM: Artificial
<220> FEATURE:
<223> OTHER INFORMATION: Artifitially synthesized target sequence for
      SiRNA

<400> SEQUENCE: 27
tgcttacaac tactgctac                                                19

<210> SEQ ID NO 28
<211> LENGTH: 19
<212> TYPE: DNA
<213> ORGANISM: Artificial
<220> FEATURE:
<223> OTHER INFORMATION: Artifitially synthesized target sequence for
      SiRNA
```

```
<400> SEQUENCE: 28
ctactgctac atgtacgag                                              19
```